(12) United States Patent
Zalameda et al.

(10) Patent No.: US 6,712,502 B2
(45) Date of Patent: Mar. 30, 2004

(54) SYNCHRONIZED ELECTRONIC SHUTTER SYSTEM AND METHOD FOR THERMAL NONDESTRUCTIVE EVALUATION

(75) Inventors: Joseph N. Zalameda, Poquoson, VA (US); William P. Winfree, Williamsburg, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/120,225

(22) Filed: Apr. 10, 2002

(65) Prior Publication Data

US 2003/0193987 A1 Oct. 16, 2003

(51) Int. Cl.[7] ............................................. G01N 25/72
(52) U.S. Cl. .............................. 374/5; 374/7; 374/124; 374/130
(58) Field of Search ............................... 374/4, 5, 6, 7, 374/124, 43, 44, 120, 121, 130, 137, 126; 250/330, 332, 341.6

(56) References Cited

U.S. PATENT DOCUMENTS

| | | | | |
|---|---|---|---|---|
| 3,401,551 A | * | 9/1968 | Maley | 374/5 |
| 3,433,052 A | * | 3/1969 | Maley | 374/126 |
| 3,451,254 A | * | 6/1969 | Maley | 374/126 |

(List continued on next page.)

OTHER PUBLICATIONS

J.G. Sun, C. Deemer and W. A. Ellingson, Thermal Imaging Measurement of Lateral Thermal Diffusivity in Continuous Fiber Ceramic Composites, Jan. 23–28, 2000. Conference Paper (7 pages).*

Kubicar, L. and Bohac, V., "Review of Several Dynamic Methods of Measuring Thermophysical Parameters," Thermal Conductivity 24 / Thermal Expansion 12, pp. 135–149 (published Jan. 11, 1999).*

Cramer et al., "The Application of Thermal Diffusivity Imaging to SIC–Fiber–Reinforced Silicon Nitride," Rev. Prog. Quant. NDE; vol. 12/B, Eds. Thompson and Chimenti, pp. 1305–1311, 1993 (no month).*

Milne, J. M; Reynolds, W. N., "Application of thermal pulses and infrared thermal imagers for observing sub–surface structures in metals and composites", SPIE vol. 590 (1985), 293–302 (1986, no month).*

Milne,J. M; Reynolds, W. N., "The non–destructive evaluation of composites and other materials by thermal pulse video thermography," Proc. SPIE vol. 520 (1984), p.119–122 (1985, no month).*

Joseph N. Zalameda, "Synchronized Electronic Shutter System (SESS) for Thermal Nondestructive Evaluation,"0 Thermosense XXIII Conference (Orlando, FL), (Apr. 16, 2001).

*Primary Examiner*—Diego Gutierrez
*Assistant Examiner*—Stanley J. Pruchnic, Jr.
(74) *Attorney, Agent, or Firm*—Kurt G. Hammerle

(57) ABSTRACT

The invention is a synchronized electronic shutter system (SESS) and method for same side and through transmission thermal analysis and inspection of a material for finding defects, corrosion, disbond defects, integrity of a weld and determination of paint thickness. The system comprises an infrared detector that acquires background images of the sample. A shutter then covers the detector and lamps rapidly heat the sample above ambient temperature. Shutters cover all lamps at the same time the shutter over the infrared detector is opened. The infrared detector acquires a series of temperature images over time radiated from the sample as the sample cools down. After collecting a series of temperature images taken by the SESS, a processed image is developed using one of the group comprising time derivative calculation, temperature normalization data reduction routine, thermal diffusivity curve fitting and averaging the series of temperature images.

68 Claims, 16 Drawing Sheets

U.S. PATENT DOCUMENTS

| | | | |
|---|---|---|---|
| 3,462,224 A | * | 8/1969 | Woods et al. ............... 374/126 |
| 3,504,524 A | * | 4/1970 | Maley ....................... 374/126 |
| 3,789,654 A | * | 2/1974 | Jones .......................... 374/43 |
| 3,862,423 A | | 1/1975 | Kutas et al. |
| 4,647,220 A | | 3/1987 | Adams et al. |
| 4,854,724 A | | 8/1989 | Adams et al. |
| 4,928,254 A | * | 5/1990 | Knudsen et al. ............ 374/43 |
| 5,287,183 A | * | 2/1994 | Thomas et al. ............ 348/571 |
| 5,302,830 A | | 4/1994 | Shivanandan |
| 5,324,944 A | | 6/1994 | Soch et al. |
| 5,413,098 A | | 5/1995 | Benaron |
| 5,562,345 A | | 10/1996 | Heyman et al. |
| 5,646,406 A | * | 7/1997 | Sporck et al. ............. 250/330 |
| 5,683,181 A | | 11/1997 | Shepard |
| 5,711,603 A | * | 1/1998 | Ringermacher et al. ....... 374/5 |
| 5,994,701 A | | 11/1999 | Tsuchimoto et al. |
| 6,133,569 A | | 10/2000 | Shoda et al. |
| 6,367,968 B1 | * | 4/2002 | Ringermacher et al. ....... 374/5 |
| 6,367,969 B1 | * | 4/2002 | Ringermacher et al. ....... 374/5 |
| 6,394,646 B1 | * | 5/2002 | Ringermacher et al. ....... 374/5 |
| 6,516,084 B2 | * | 2/2003 | Shepard ..................... 250/332 |
| 6,517,238 B2 | * | 2/2003 | Sun et al. .................... 374/43 |
| 6,542,849 B2 | * | 4/2003 | Sun ........................... 702/172 |

* cited by examiner

PROCESSED IMAGE

TEMPERATURE IMAGE

PROCESSED IMAGE WITH FILTER

TEMPERATURE IMAGE WITH FILTER

PROCESSED IMAGE WITH SESS

TEMPERATURE IMAGE WITH SESS

PROCESSED IMAGE WITH SESS

PROCESSED IMAGE WITHOUT SESS

PROCESSED IMAGE WITH SESS

PROCESSED IMAGE WITHOUT SESS

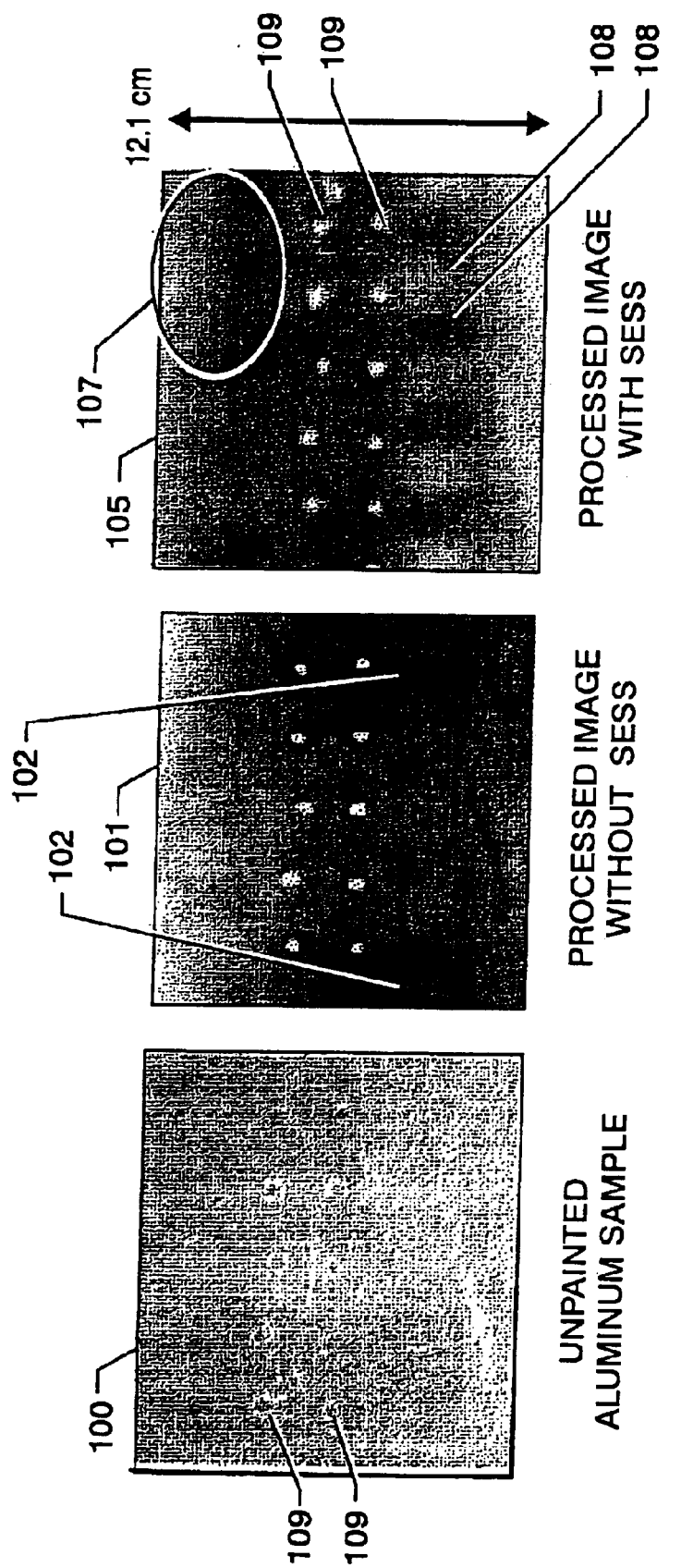

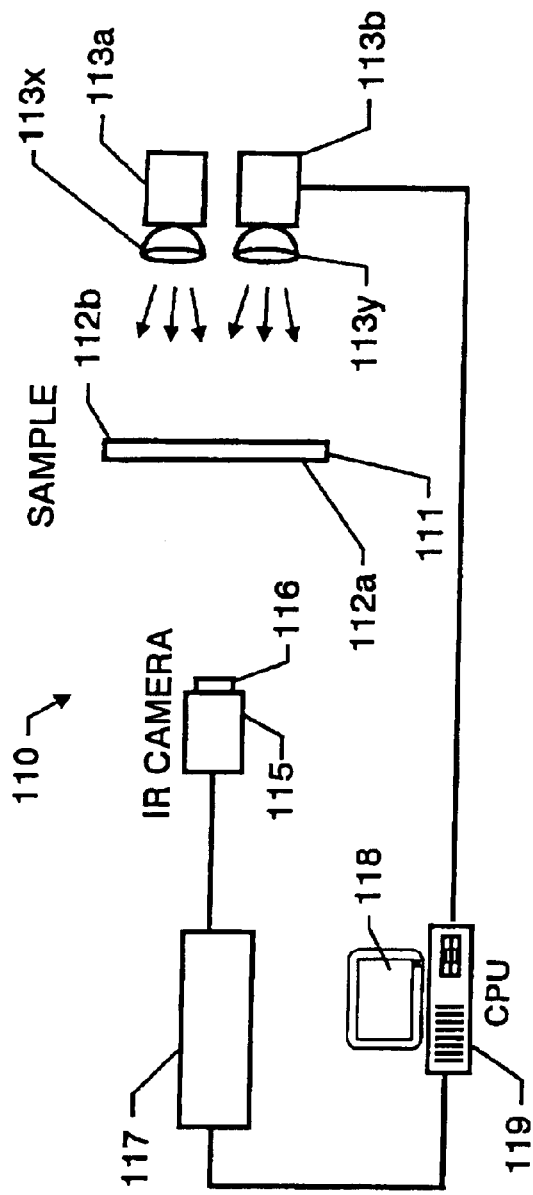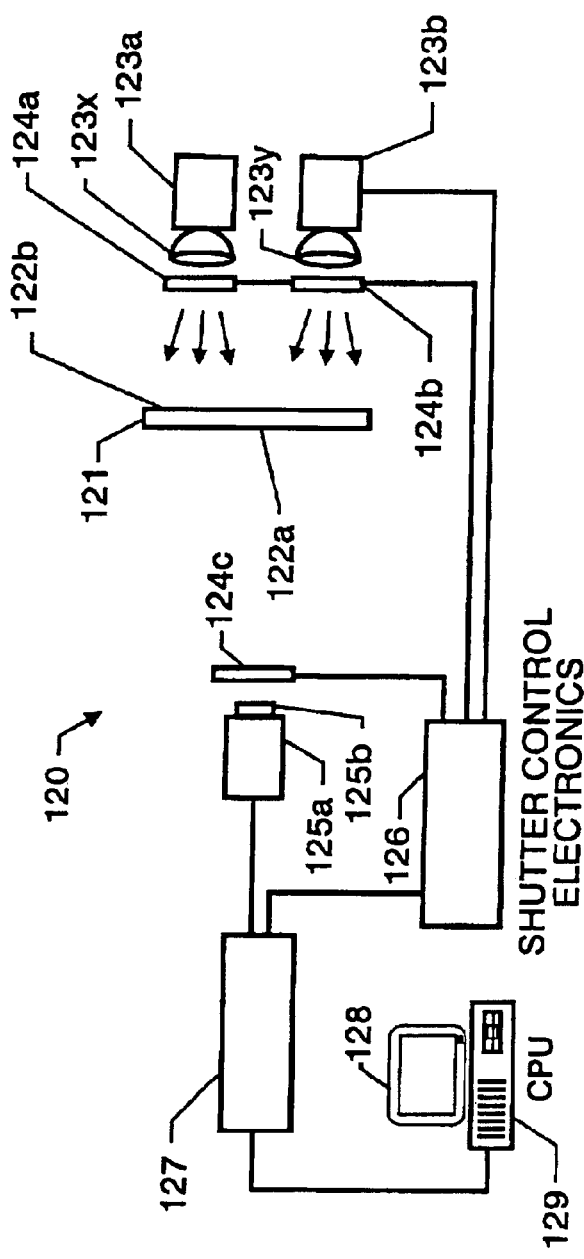
PRIOR ART
FIG. 11
FIG. 12

THROUGH TRANSMISSION TEMPERATURE IMAGE WITHOUT SHUTTER

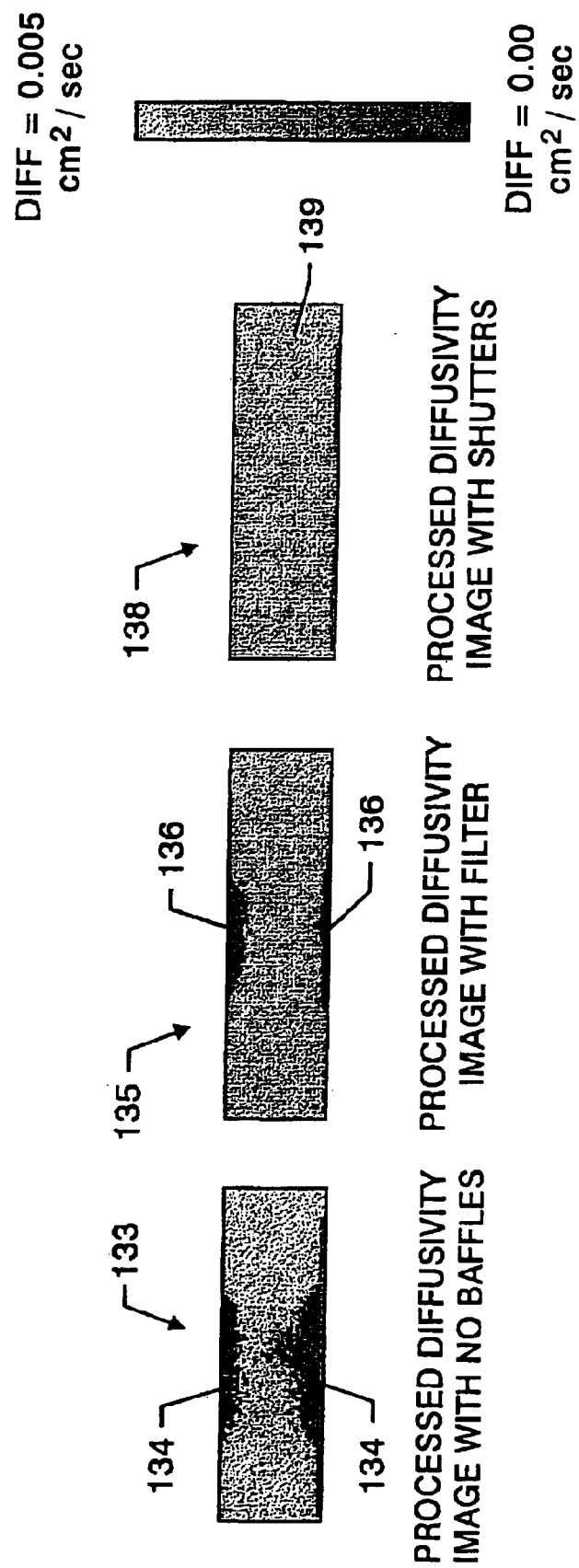

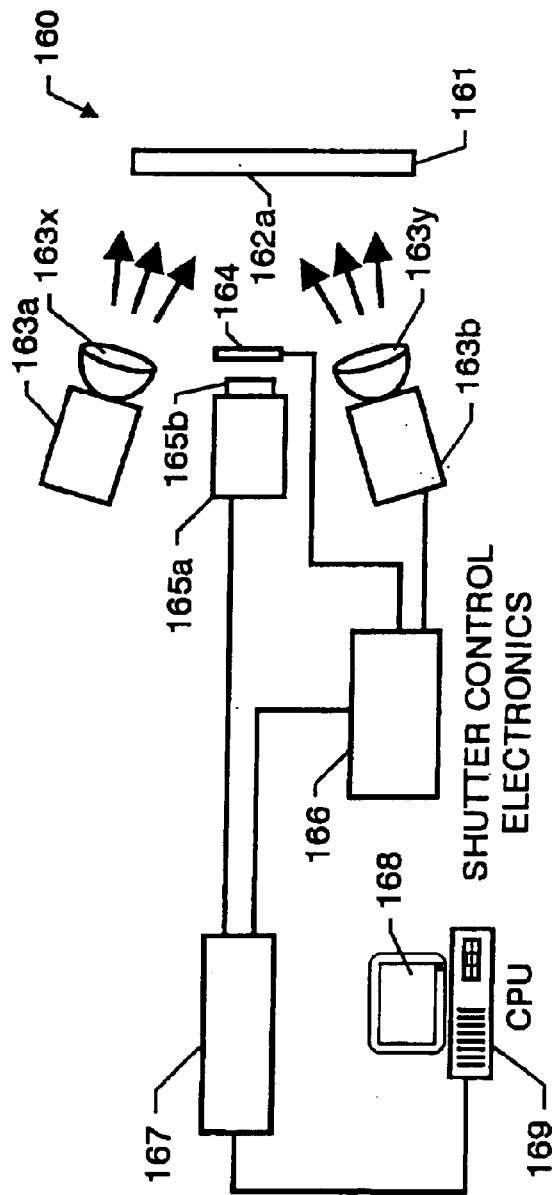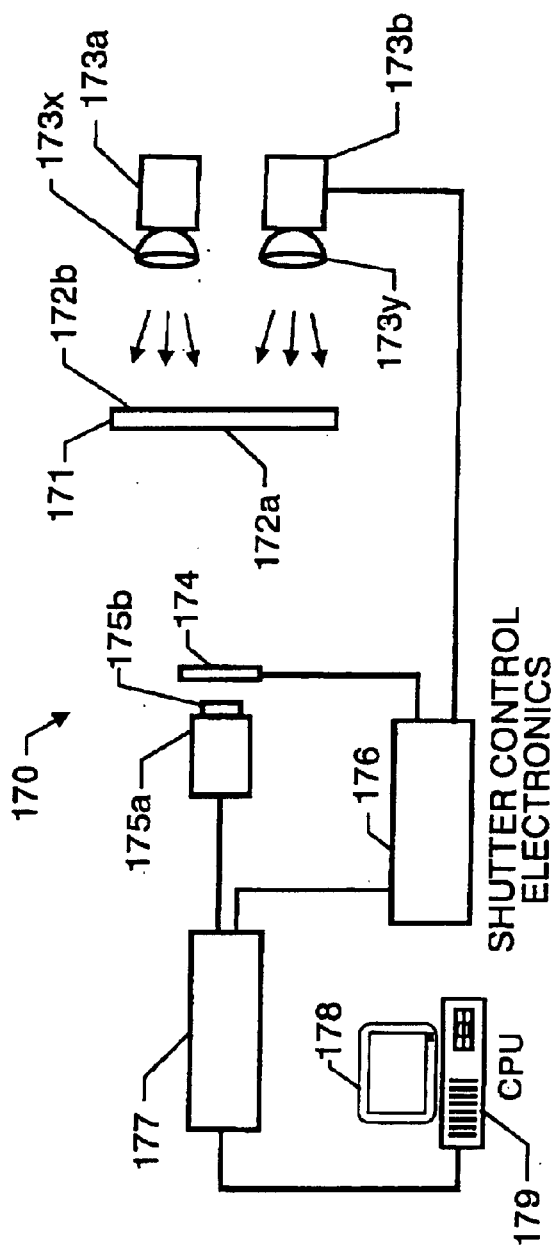
FIG. 16
FIG. 17

SYNCHRONIZED ELECTRONIC SHUTTER SYSTEM AND METHOD FOR THERMAL NONDESTRUCTIVE EVALUATION

ORIGIN OF THE INVENTION

The invention described herein was made by employees of the United States Government and may be manufactured and used by or for the Government for governmental purposes without the payment of any royalties thereon or therefor.

1. Field of the Invention

This invention pertains to a method and apparatus of thermal, non-destructive inspection of the surface of a material.

2. Background of the Invention

Thermal, non-destructive inspection systems are an inspection tool for both manufacture and in-service applications. These inspection systems are based on the application of heat onto the surface of the structure to be inspected. Typical heat sources used are flash lamps. The short duration intense light is absorbed by the surface to be inspected and a temperature rise above ambient temperature is produced. A device such as in an infrared detector is used to measure small differences in the surface temperature as the sample cools down. The temperature time history is recorded and stored for analysis using theoretical models. Model based thermal inspections are possible when extraneous factors are minimized so that the theoretical models best fit the data.

Thermal inspection of a sample material can be achieved by single-sided inspection or by through-transmission inspection. Single-sided inspection means that the flash lamps that heat the sample under test are on the same side of the sample as the infrared detector that thermally inspects the temperature of various points on the sample versus time as the sample cools down after being heated. Through-transmission inspection requires that the infrared detector be on a side of the sample under test opposite to the flash heat lamps used to heat the sample. Through-transmission measurements can utilize either one or more flash heat lamps for thermal inspection, depending on the size of the sample.

Measurements gleaned from thermal inspection generally include locating defects, including disbond defects in a sample under test, integrity of a weld on an aircraft, the detection of corrosion and the detection of paint thicknesses. The detection of corrosion is found by determining the volumetric heat capacity on all points of a sample under test (specimen) gleaned from data received by an infrared detector that is processed based on a theoretical model. The location of defects is determined by examining a thermal diffusivity image obtained by processing the specimen's thermal responses. The thermal diffusivity is defined as the ratio between the thermal conductivity of the sample under test divided by the volumetric heat capacity of the sample under test. Generally, these measurements are made by first rapidly heating the sample under test by one or more flash lamps, then measuring the rate of cool down over time on different points of the sample under test by an infrared detector.

SUMMARY OF THE INVENTION

The invention is a thermal, non-destructive evaluation system and method comprising a synchronized electronic shutter system (SESS) where each flash heat lamp and a detector for measuring infrared thermal energy such as an infrared camera all contain shutters. The opening and closing of each shutter is electronically controlled so that the data read when the shutter for the infrared detector is opened is both accurate and precise, whether it be for single-sided thermal inspection or for through-transmission inspection. Upon receiving a signal from a source like a computer to conduct a thermal inspection of an object under test, the shutter to the infrared detector is opened while the shutter(s) to the flash heat lamp(s) is/are closed, enabling the infrared detector to acquire background images for the object under test. Following this activity, the shutter to the detector is closed at the same time the shutter(s) to the flash heat lamp(s) is/are opened. While the shutter(s) to the flash heat lamp(s) is/are open and the shutter to the infrared detector is closed, the flash heat lamp(s) are fired or actuated (flash duration is typically 0.008 seconds) to heat the object under test. Because the shutter to the infrared detector is closed, photons reflected off the object under test do not influence the infrared detector. Also, because the shutter(s) of the flash heat lamp(s) is/are open, the/these shutter(s) is/are not heated. After actuation of the flash heat lamp(s), the shutter(s) on the flash heat lamp(s) is/are closed to cover the flash heat lamp(s) at the same time the shutter to the infrared detector is opened to start thermal data acquisition over a period of time while the object under test cools down. Because the shutter(s) to the flash heat lamp(s) now cover the flash heat lamps, residual transient effects originating from a recently fired flash heat lamp(s) do not reach the infrared detector and thus do not effect the data being acquired. Also, because the shutter(s) for the flash heat lamp(s), which may be made from a material having high thermal conductivity, was/were not covering the flash heat lamp(s) during actuation, the shutter(s) over the flash heat lamp(s) are cool, thus eliminating the erroneous effects of infrared radiation emanating from a material that covers the flash heat lamp(s) and being reflected off the object under test and back into the infrared detector. The method of this invention uses an SESS that operates the detector shutter and the flash heat lamp shutter(s) so as to complement each other during times of opening and closing.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein:

FIG. 10A is an unpainted aluminum sample partially adhered to an aluminum metal stiffener to be used in disbond thermal inspection experiments;

FIG. 10B is a processed image of the sample of FIG. 10A using the system of FIG. 1;

FIG. 10C is a processed image of the sample of FIG. 10A using the SESS embodiment of FIG. 5;

FIG. 11 illustrates a through-transmission thermal inspection system using two flash heat lamps to heat a sample under test;

FIG. 12 illustrates an embodiment for a synchronized electronic shutter system (SESS) for through-transmission thermal inspection using two flash heat lamps in accordance with the present invention;

FIG. 13B is a processed image using a series of temperature images of FIG. 13A wherein only one flash heat lamp without a filter is used;

FIG. 13C is a processed image using the system of FIG. 11 wherein the filter covers a single flash heat lamp, the processed image being obtained from a series of temperature images like the image of FIG. 13A;

FIG. 13D is a thermal diffusivity processed image acquired by utilizing the SESS embodiment of FIG. 12;

FIG. 13E illustrates how thermal diffusivity in cm$^2$/sec varies with gray scale shading of a processed image between 0.000 and 0.005 cm$^2$/sec;

FIG. 16 illustrates another embodiment for the SESS with a single-sided setup;

FIG. 17 illustrates another embodiment for the SESS using through-transmission.

DETAILED DESCRIPTION OF THE INVENTION

Figure 1:
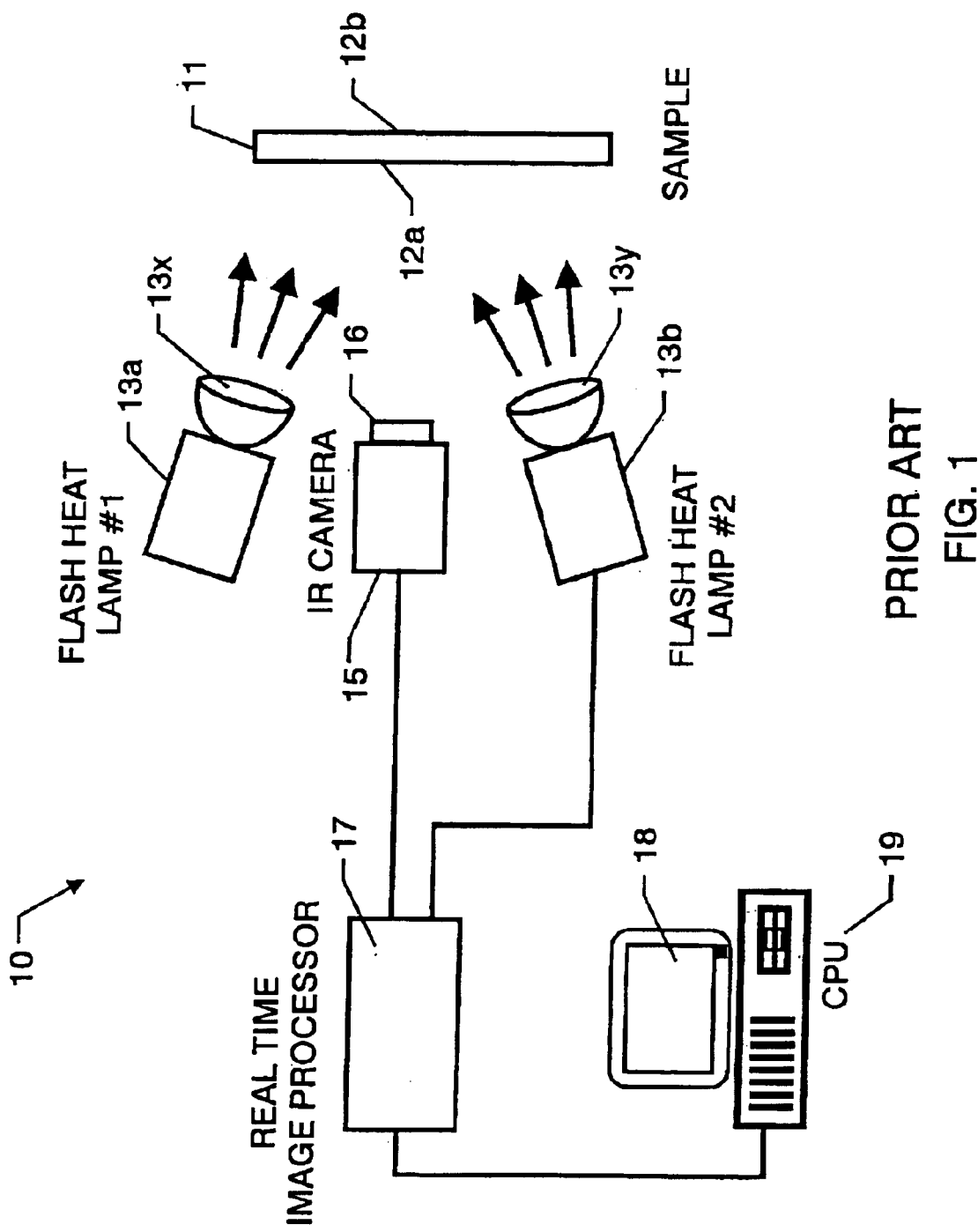
FIG. 1 shows a single-side thermal inspection system setup using two flash heat lamps to heat a sample under test.

Referring now to the drawings, FIG. 1 illustrates a thermal inspection system 10 for single-side inspection, in accordance with the related art. The thermal inspection system in FIG. 1 has a thin sample 11 having two surfaces 12a and 12b opposite to each other, a first flash heat lamp 13a and a second flash heat lamp 13b, each having reflectors that point towards surface 12a of sample 11. Two flash lamps are generally used in same side thermal inspection systems to provide more even heating across the surface 12a of sample 11 and to provide a larger temperature rise of sample 11 than if just one flash lamp were used. First flash heat lamp 13a has a reflector 13x that is pointed at surface 12a of sample 11. Similarly, second flash heat lamp 13b has a reflector 13y that is also pointed at surface 12a of sample 11. An infrared detector 15 having a lens 16 is pointed towards surface 12a of sample 11 to acquire thermal data as a function of elapsed time as sample 11 cools down after being heated by firing flash lamps 13a and 13b. Image processor 17 serves to process raw temperature data acquired by infrared detector 15 to form a processed image used in thermal inspections. Computer 18 having a central processing unit 19 works with image processor 17 to store raw temperature data captured by infrared detector 15 over time and then forms a processed image therefrom.

Figure 2:
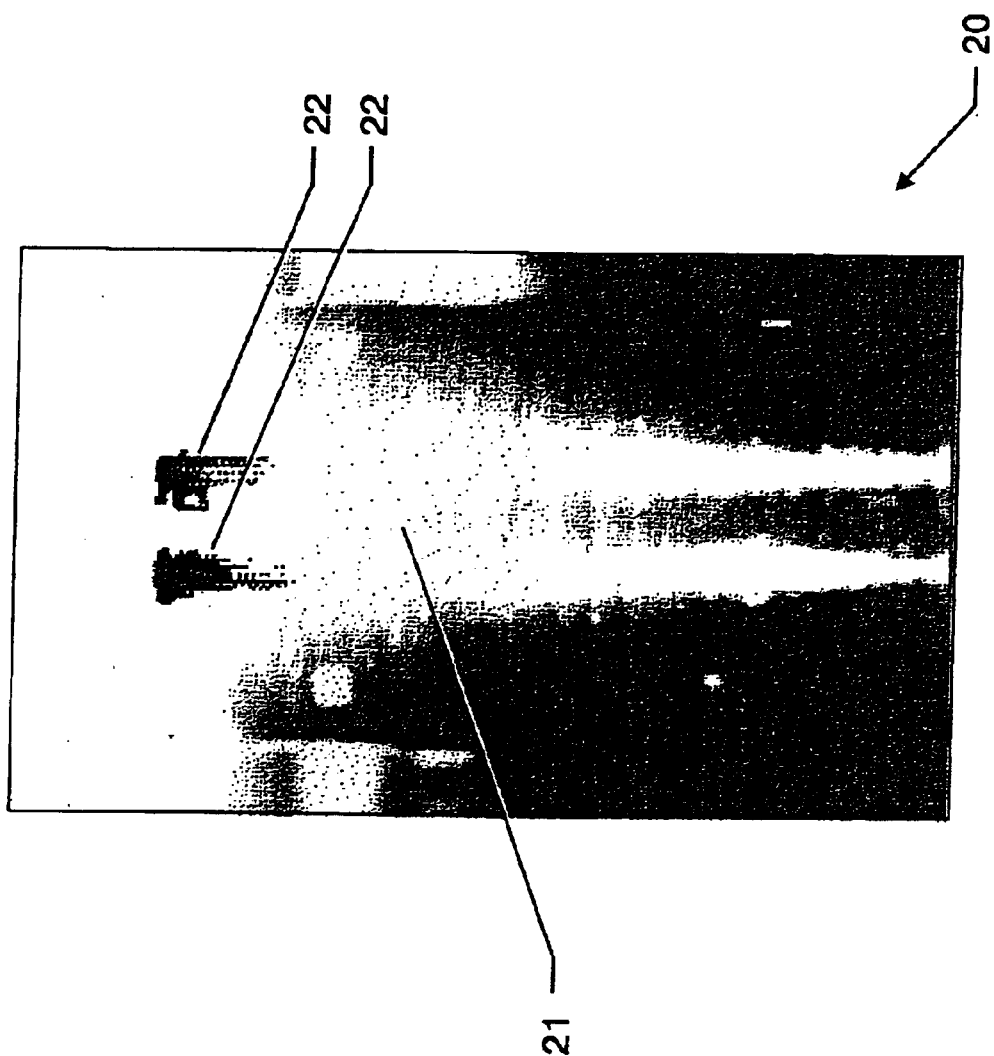
FIG. 2 illustrates a temperature image taken by the system of FIG. 1 illustrating saturation of detectors.

The single-sided thermal inspection system of FIG. 1 is problematic for several reasons. In particular, the effect of the flash lamps on the infrared detector is a cause of major concern. For example, the system of FIG. 1 has a tendency to expose the detectors of the detector to a high intensity flash caused by the reflection of infrared photons off the sample under test. This reflection causes distorted temperature measurements of the sample under test. This distortion is illustrated in FIG. 2 which is a temperature image 20 having a reflected flash 21 that results in saturated pixels 22. The saturated pixels 22 are caused by the surface emissivity of the sample 11 not being a perfect absorber of all the incident infrared photons. The light intensity must be high in order to heat the structure sufficiently. Because of the high amount of infrared photons, some are reflected back into the infrared camera's detectors and saturate the temperature image.

For cooled quantum detectors (infrared energy is detected by counting the number of photons absorbed), this saturation appears not to be as much of a problem because the saturated state of the detectors is temporary for one image cycle. Some newer infrared imagers use detectors that are based on thermal detector technology where the infrared energy is detected by the photons causing a temperature change on the detector element. Saturation of these detectors could result in residual thermal effects on the detectors thus potentially effecting the measurement over a number of image data cycles. This saturation would introduce unknown and uncorrectable errors when comparing the data to a model. By shielding the detector during the flash, the camera is not exposed to the high intensity photons but rather only the surface temperature of the sample under test.

The raw data taken by the infrared detector is processed to produce a temperature image. The temperature image is about 0.03 seconds of exposure of the infrared detector 15 to sample 11. Image processor 17 can take a series of temperature images over time from infrared detector 15 and produce a processed image.

The method used to form a processed image from a series of temperature images often depends on the circumstances. To measure and image thermal diffusivity, a series of temperature images are sent through a curve fitting routine like the one in equation 1 in the discussion of FIG. 13D below. Because volumetric heat capacity and thermal conductivity are related to thermal diffusivity, these other two quantities may be imaged by imaging the thermal diffusivity. Thermal diffusivity is used most often to look for defects in a material. In corrosion detection and disbond defect (delamination), temperature normalization data reduction routines may be used to process a series of temperature images into a final, processed image. Another form of processing a series of temperature images is through time derivative calculations. This technique is also used to detect the location of a defect on a sample under test. Finally, the technique of averaging can also be used to process an image from a time-sequenced series of temperature images to find a defect.

Figure 3B:
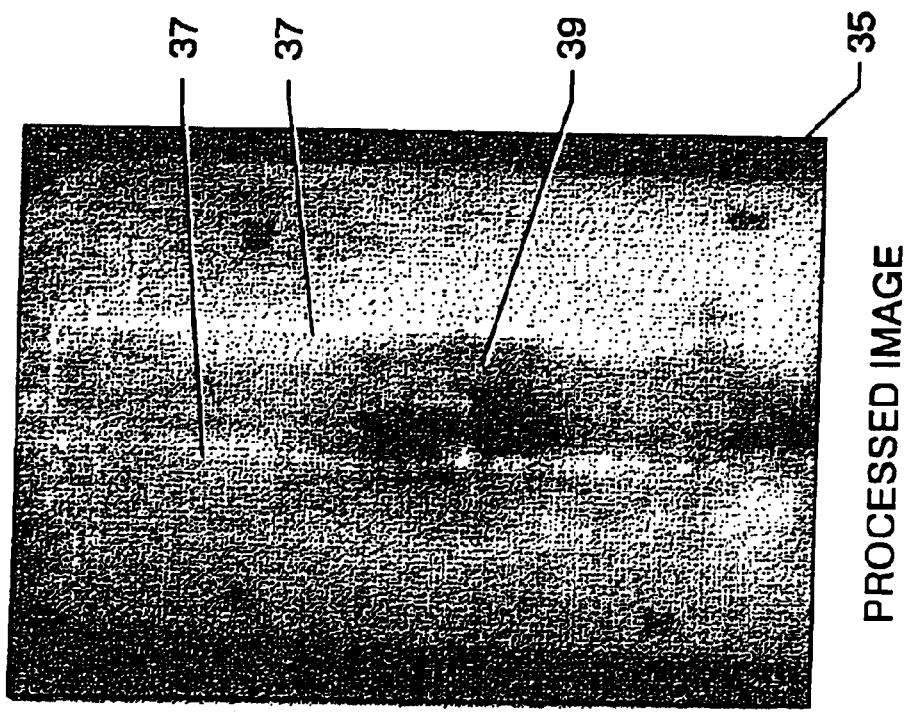
FIG. 3B illustrates the processed image of a series of temperature images like the image of FIG. 3A.
Figure 3A:
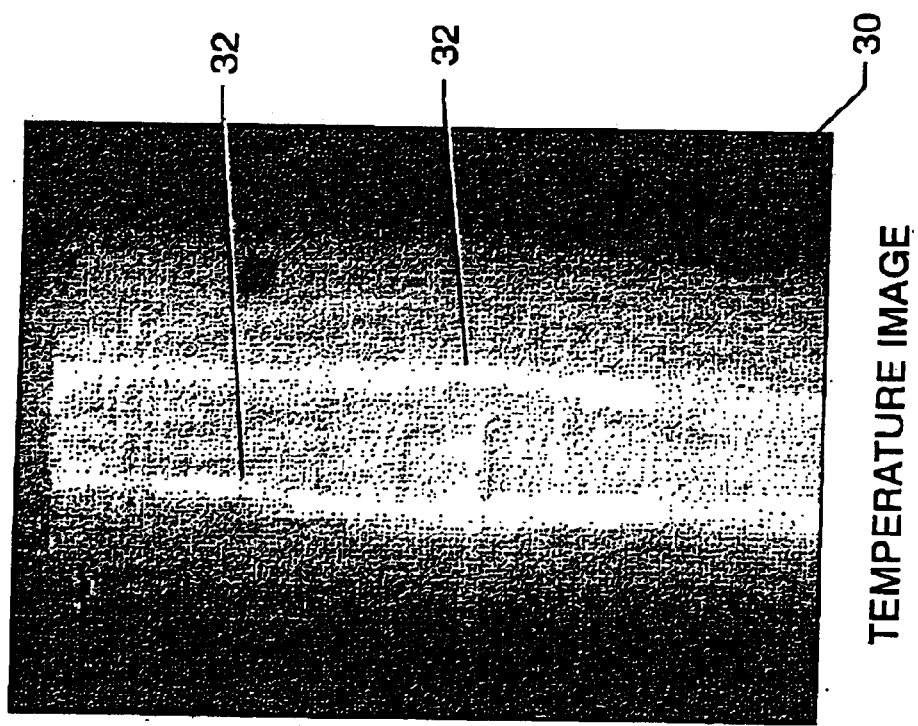
FIG. 3A illustrates a temperature image of a sample taken by the system of FIG. 1 when the temperature image is taken after the firing of the flash heat lamps.

Another concern of a single-sided thermal inspection system besides flash heating is the residual effect of the flash lamps. The high luminance flash is produced with a flash tube that discharges a high voltage capacitor in a short period of time. This type of flash system usually has a fan cooler within it to minimize the temperature rise. As a result of the residual cooling, the flash head introduces a transient thermal response (infrared radiation) that is reflected off the sample under test and back into the detector. Although this afterglow is not visible to the naked eye, the lamps, being recently fired, are hot and emit infrared radiation that is reflected off the sample under test. This reflected radiation superimposes with infrared radiation emanating from the sample under test back into the infrared detector and gives erroneous results. This afterglow phenomenon is illustrated in FIGS. 3A and 3B. The sample for this thermal inspection is a composite aluminum cylinder comprising graphite epoxy with wound filaments as the outer shell. As illustrated in FIGS. 3A and 3B, the transient, residual infrared radiation is superimposed on the thermal inspection data acquired from the sample under test. The resultant temperature image (i.e., having a duration of 0.03 seconds) at a point in time sometime shortly after the firing of the flash lamps is illustrated in the temperature image 30 of FIG. 3A having residual lamp reflections 32.

FIG. 3B is a processed image taken from a series of about 200 temperature images like the image 30 of FIG. 3A taken after the firing of the flash lamps, 13a, 13b and then processed by way of time derivative calculations into the processed image 35 of FIG. 3B. The processed image 35 also illustrates the effects of infrared radiation emanating from the flash lamps after being fired and reflected off the sample and back into the detector to result in lamp reflections 37 in the processed image of FIG. 3B. The unwanted radiation reflected off the sample under test can usually be seen as a slowly fading pattern of the flash head reflected on the sample into the detector. Even for high emissivity surfaces where the surface is painted, the effect of residual, transient radiation emanating from a recently fired flash lamp reflected off the surface of the sample under test and back into the infrared detector can still produce unacceptable results. The transient nature of the flash head cool down is not known and the degree of error captured by the infrared detector would be dependent on the surface emissivity of the sample as well as on characteristics of the flash heat lamps themselves. To capture the image of a defect on the surface of a sample under test, a time derivative calculation is applied to the set of temperature images to result in a processed image 35 as illustrated in FIG. 3B. Processed image 35 illustrates both the defect 39 and the residual effect from the flash lamp 37.

Filters made of a transparent, thermoplastic polymer such as Plexiglas™ are sometimes used to shield the heat radiating from flash lamps. The transmission characteristics of the filter allows for transmission of optical wavelengths used for heating and suppresses the infrared wavelengths emitted when the flash heat lamps cool down after recently being fired. Using the system of FIG. 1, a filter using a 0.065" thick piece of Plexiglas™ to cover each flash heat lamp produces the temperature image 40 of FIG. 4A. Note again the presence of residual lamp reflections 42 generated by the filters that are heated by the firing of the flash lamps. The filters reduce the amount of erroneous radiation that reaches the infrared detector, but do not entirely eliminate it.

Figure 4B:
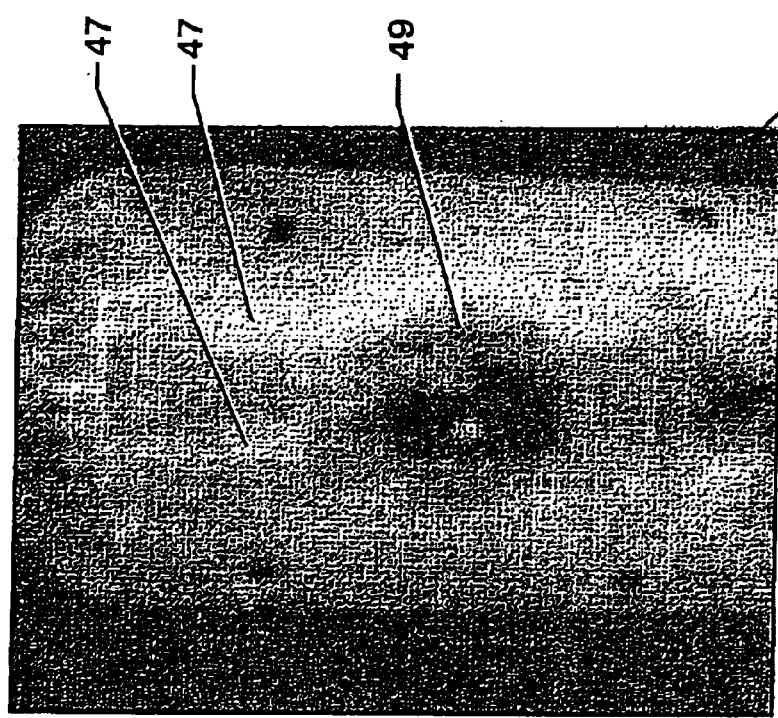
FIG. 4B illustrates the processed image of a series of temperature images like the image of FIG. 4A.
Figure 4A:
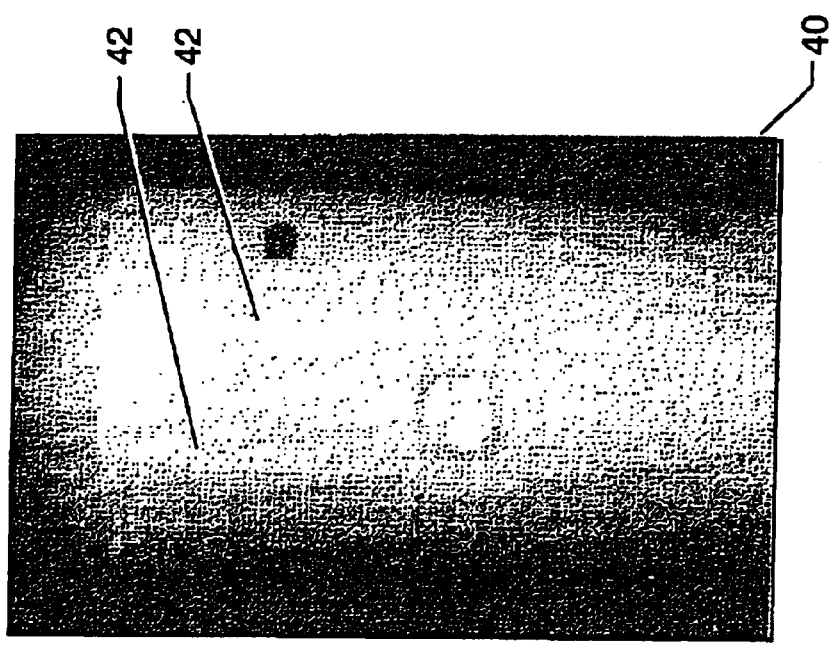
FIG. 4A illustrates the temperature image taken by the system of FIG. 1 where a filter covers each flash heat lamp.

FIG. 4B is a processed image 45 using filters to cover the flash lamps of FIG. 1, wherein the sample is a composite aluminum cylinder including graphite epoxy with wound space filaments as the outer shell. The processed image 45 comprises a reduction of a series of approximately 200 temperature images, each image taken after the firing of the flash heat lamps and each temperature image having a 0.03 second duration. A time derivative calculation is applied to the series of images to produce the processed image. FIG. 4B still contains the lamp reflections 47 resulting from the heated filter as they reflect off the sample and back into the infrared detector after the firing of the flash heat lamps. The reason for erroneous data in FIGS. 4A and 4B is the heating of the filter. The filter is in the line of fire of the flash lamp and therefore heats up. The heat radiating from the hot filter becomes a source of unwanted infrared radiation that reflects off the sample and back into the detector. Therefore, when a filter is used in a single sided setup to cover the flash heat lamps, the infrared detector acquires a superposition of both the thermal inspection data of the sample under test and the unwanted infrared radiation originating from the heated filter and reflected off the sample under test. Similarly, another drawback to using a filter is the amount of heat being delivered to the sample is less than if filters were not used. As a result, use of filters results in a poorer signal-to-noise ratio. Nevertheless, as with FIG. 3B, the defect 49 can be seen from processed image 45 as a dark spot 49.

Figure 5:
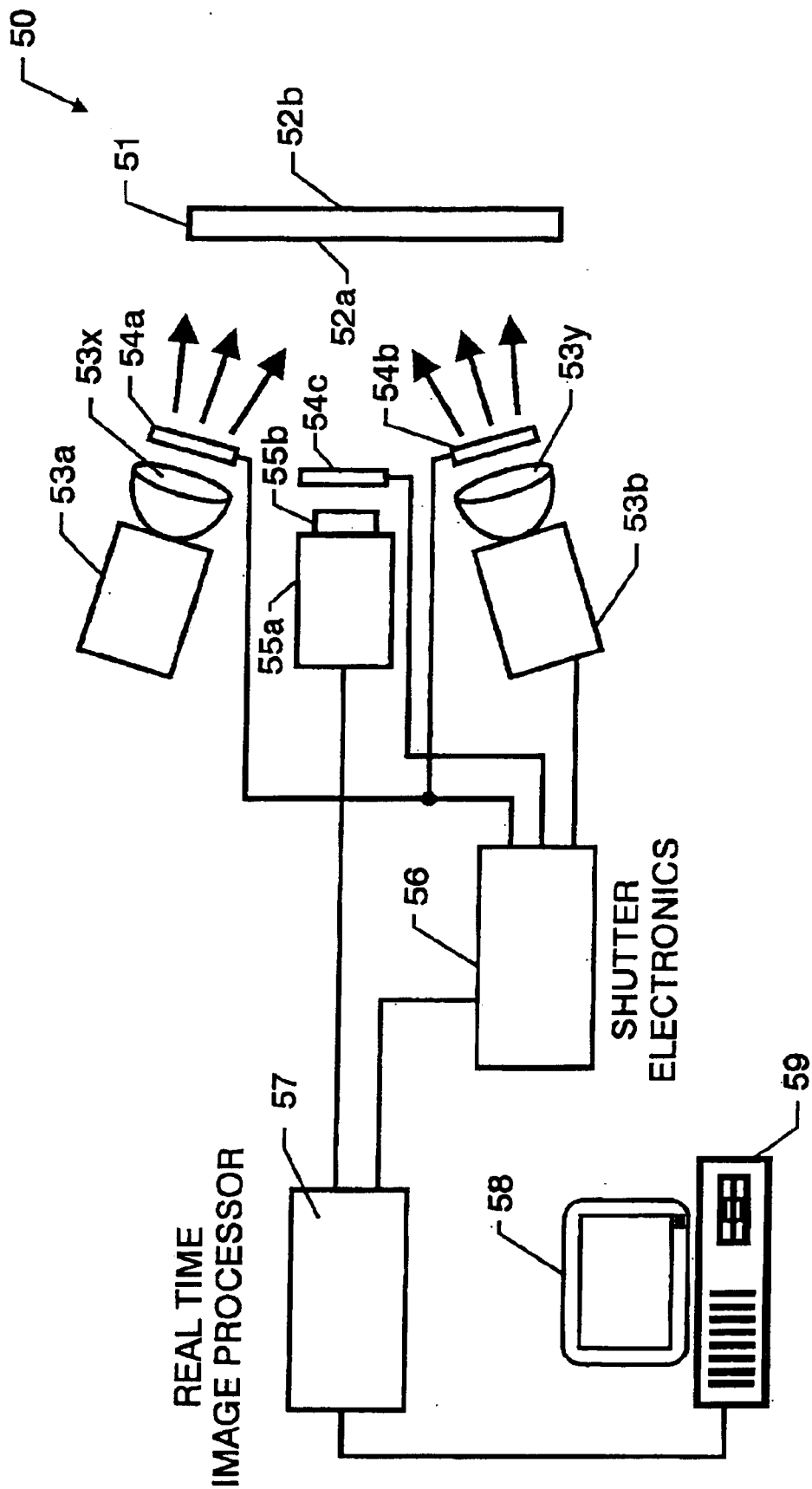
FIG. 5 illustrates one embodiment for a synchronized electronic shutter system (SESS) for single sided thermal inspection using two flash heat lamps according to the present invention.

Referring now to FIG. 5, one embodiment of a synchronized electronic shutter system (SESS) 50 is shown for a single-sided inspection in accordance with the present invention. The system 50 is similar to the system 10, but system 50 comprises shutters 54a, 54b and 54c capable of covering first means for heating 53a, a second means for heating 53b and lens 55b of infrared detector 55a, respectively. In addition, system 50 comprises shutter electronics 56 that control the timing for the opening and the closing of each of the shutters 54a, 54b and 54c along with the timing of firing first means for heating 53a and second means for heating 53b (if used). The synchronization in this system 50 accounts for the time the shutters need to mechanically open and close before the firing of the means for heating. The system 50 has no delay, however, between sending a signal to fire a means for heating and the actual firing it. The shutter electronics 56 will be described in more detail during the discussion of FIG. 15.

Reflector 53x of first means for heating 53a is pointed at surface 52a of sample 51 and is covered by shutter 54a. Similarly, reflector 53y of means for heating 53b is pointed towards surface 52a of sample 51 and is covered by shutter 54b. Infrared detector 55a may comprise an infrared camera or other means of detecting infrared energy. The detector has a lens 55b that is also pointed at surface 52a of sample 51 and can be covered by shutter 54c. The system 50 has an image processor 57 electrically connected to computer 58 having a central processing unit 59 to convert temperature images gleaned from infrared detector 55a into a processed image that better illustrates corrosion, defects, disbond, delamination and paint thickness in sample 51.

The first and second means for heating 53a, 53b may comprise a first flash heat lamp and a second flash heat lamp.

Alternatively, the means for heating may comprise a quartz lamp or other heat source capable of heating the sample under test 51 to a temperature above ambient temperature in quick fashion. For purposes of this detailed description and the appended claims, the term "lamp" will include any such heat source equivalent to a flash heat lamp, a quartz lamp, or other heat source.

The shutters 54a, 54b, and 54c may comprise one of a variety of mechanical structures, including a roller blind with a slot, a rotating disc with a slot, an iris diaphragm, a circular eyelid device, a set of movable vanes, or any other device capable of obstructing the transmittal of radiation along a directed path. The shutters may comprise all being the same mechanical structure or any combination of the variety just listed. The shutters 54a, 54b, and 54c may be made of a reflective material and may also be made of a material having with low-emissivity properties.

The embodiment of FIG. 5, if operated according to the method of the present invention, will provide thermal image data and processed image data that (1) reduces erroneous superimposed radiation from reaching the lens of the infrared detector, (2) provides a processed image that converges with theoretical models, and (3) provides a processed image that clearly identifies defects, corrosion, and other problems with the sample under test while significantly reducing unwanted and erroneous radiation into the lens of the infrared detector.

The system 50 operates as follows. Before firing the lamps, 53a and 53b, the shutter 54c over the detector 55a is opened to acquire the necessary background data frame for offset calibration. During flash heating, the shutter 54c over the detector is closed to prevent the photons from the high intensity lamp from entering the infrared inspection detector and shutters 54a and 54b covering reflectors 53x, 53y to the heat lamps 53a, 53b, respectively, are opened. The flash heating duration is short (about 0.008 seconds) and heats the sample under test by approximately 10 degrees Celsius above the ambient temperature. Immediately after the lamps 53a, 53b are fired, the detector shutter 54c is opened to measure the surface temperature while shutters 54a, 54b, close over lamps 53a, 53b, respectively. This shuttering and data collecting process is synchronized to the start of the acquisition of the next detector data frame. The shutters 54a, 54b that are placed over the reflectors of lamps 53a, 53b block the infrared heat radiating from the respective lamp after heating. The shutters 54a, 54b are synchronized electronically with the detector shutter 54c to close when the detector shutter opens and vice versa.

Figure 6B:
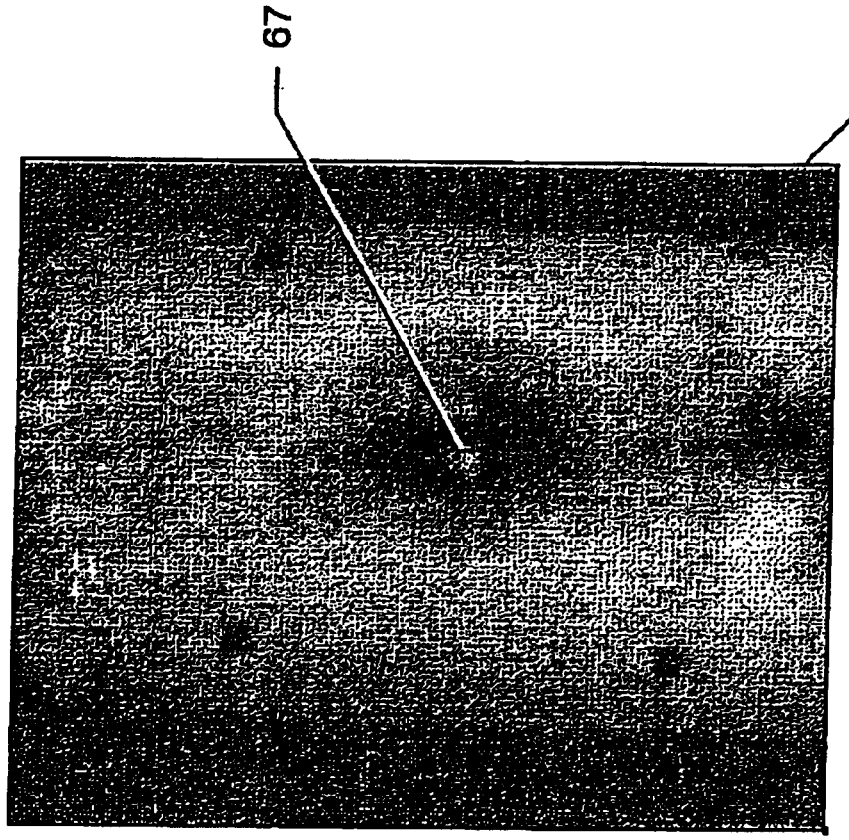
FIG. 6B is a processed image generated by a series of temperature images like the image of FIG. 6A using the SESS embodiment of FIG. 5.
Figure 6A:
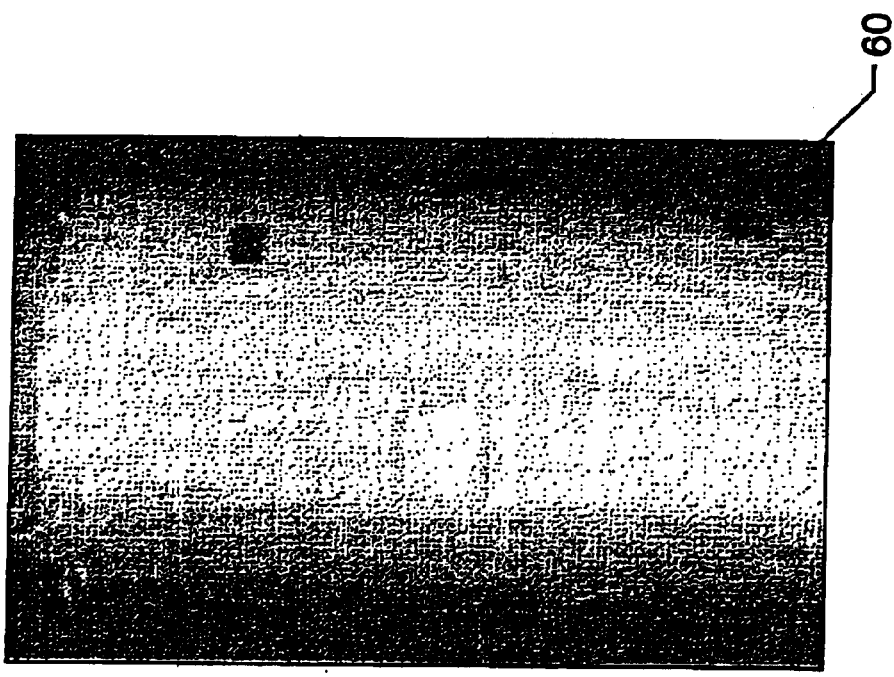
FIG. 6A is a temperature image of a sample using the SESS embodiment of FIG. 5.

Using the setup shown in FIG. 5, some results of the single-side measurements are shown in FIGS. 6A and 6B. Referring to FIGS. 6A, a single temperature image 60 using the system 50 with a pair of flash heat lamps is shown for the same test sample used for FIGS. 3A and 4A. Referring to FIG. 6B, a processed image 65 is obtained by applying the same time derivative calculation discussed earlier for FIGS. 3B and 4B to a series of the temperature images 60 over time. Note that FIG. 6B clearly displays a defect 67 as a dark spot on the processed image 65 as opposed to the non-SESS processed images of FIGS. 3B and 4B.

Figure 8:
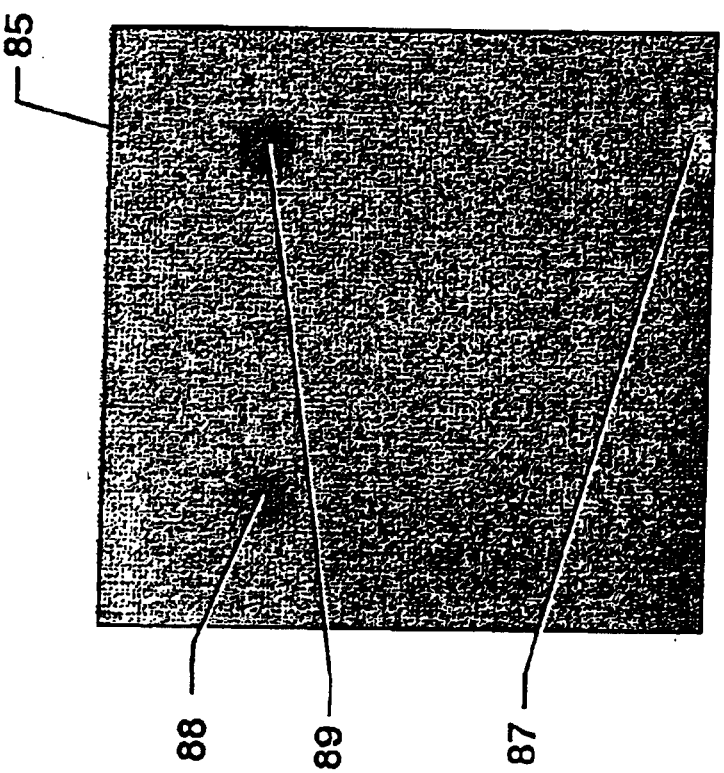
FIG. 8 illustrates a processed thermal image for the same sample of FIG. 7 using the SESS embodiment of FIG. 5.
Figure 7:
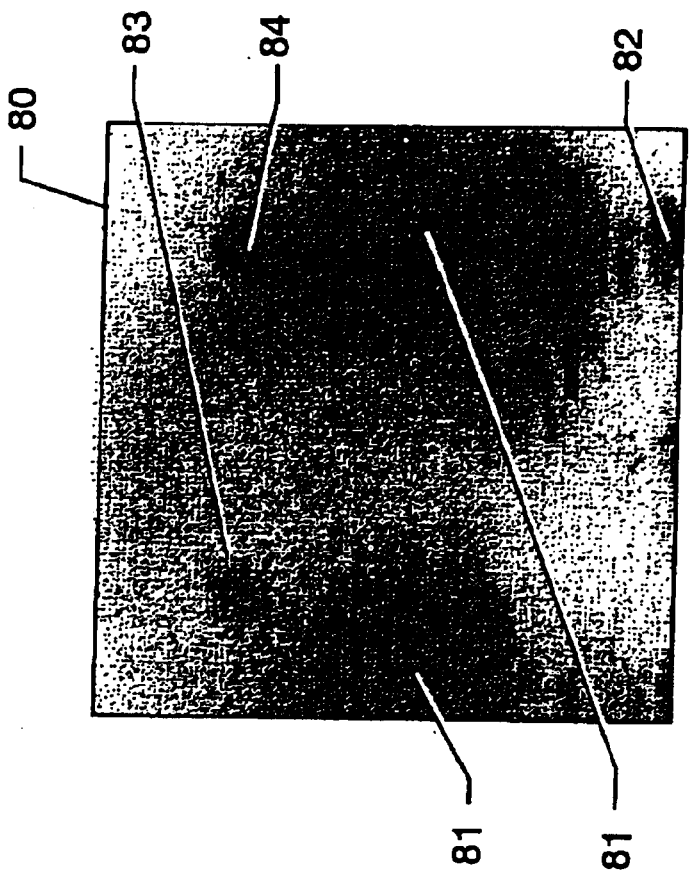
FIG. 7 illustrates a processed thermal image for a test sample exhibiting both 7.5% and 12.5% aluminum corrosion samples using the system of FIG. 1.

As shown in FIGS. 7 and 8, a comparison is made between the processed thermal image 80 without SESS and with SESS, using the processed thermal image systems of FIGS. 1 and 5 respectively. The test sample was a flat plate having 7.5 and 12.5 percent corrosion. The effect of the lamps are clearly seen in FIG. 7 as dark areas 81 that can actually mask the corrosion area. Reference numeral 82 indicates paint variation thickness on the processed image 80 and reference numeral 87 indicates paint thickness variation on the processed image 85. Reference numeral 83 indicates the 7.5% corrosion on the image 80 and reference numeral 88 indicates the 7.5% corrosion on the image 85. Reference numeral 84 indicates the 12.5% corrosion of image 80 while reference numeral 89 indicates the 12.5% corrosion of image 85. By comparing FIG. 7 with FIG. 8, processed image 80 clearly shows the superposition of flash lamp effects 81 while processed image 85 using the SESS with a pair of flash lamps does not. Also, the 7.5%, 12.5%, and the paint thickness variations are more pronounced in processed image 85 than in image 80.

Figure 9B:
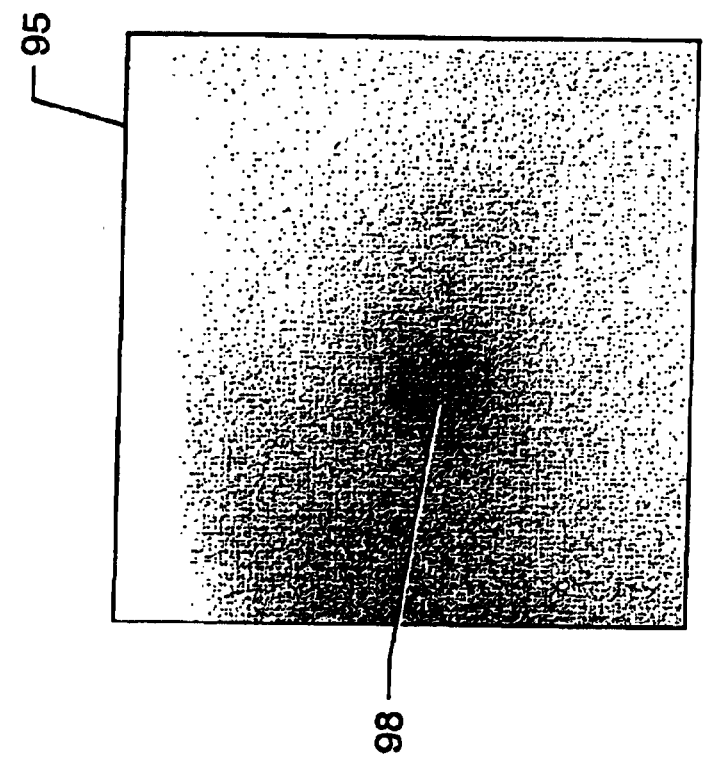
FIG. 9B illustrates a processed thermal image for the same sample of FIG. 9A using the SESS embodiment of FIG. 5.
Figure 9A:
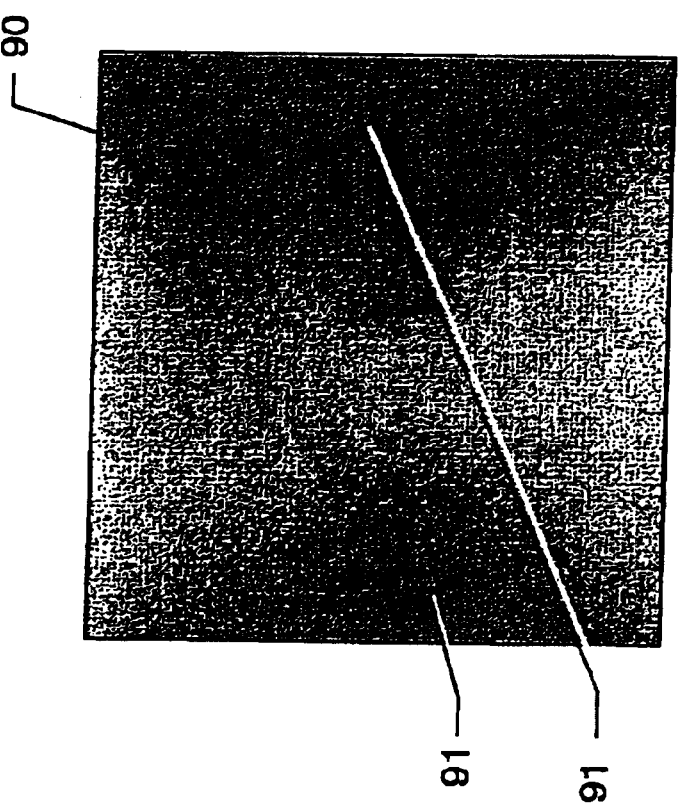
FIG. 9A illustrates a processed thermal image for a 2.5% aluminum corrosion sample using the system of FIG. 1.

The differences in results of a processed image with and without SESS are even more pronounced for the detection of 2.5% corrosion defects. A comparison of the processed thermal images for a test sample having 2.5 percent corrosion is shown in FIGS. 9A and 9B. The field of view for these two figures is 6.35 cm, which is smaller than the field for FIGS. 7 and 8. The processed image 90 in FIG. 9A is acquired using the system of FIG. 1 and the processed image 95 in FIG. 9B is acquired using the system 50 with a pair of flash heat lamps. The sample of FIGS. 7, 8, 9A, and 9B was 0.102 centimeters thick with a 1.27 centimeters diameter and had circular material loss regions of 0.0025, 0.0076, and 0.0127 centimeters in thickness for corrosion values of 2.5, 7.5, and 12.5 percent. The measurement parameters were 120 frames acquired at a camera frame rate of 60 Hertz. The processing of these 120 frames was a temperature normalization data reduction routine. FIG. 9A clearly illustrates the flash lamp superposition effects 91 but does not distinguish the 2.5% corrosion defect, rendering the corrosion undetectable. On the other hand, the processed image 95 of FIG. 9B clearly illustrates the 2.5% corrosion defect as a dark spot 98 on image 95.

Another use for SESS thermal inspections is to locate a disbond defect on an uncoated aluminum sample having an aluminum metal stiffener bonded to it. Disbond generally refers to delamination or any breaching of an adhesive used to bond two surfaces together. A location of breaches in the adhesive between two surfaces is called an area having a disbond defect.

Referring to FIGS. 10A–10C, thermal inspections were performed on an uncoated aluminum sample with an aluminum metal stiffener bonded to the backside. FIG. 10A is a photograph of the unpainted aluminum sample 100 used in FIGS. 10B and 10C. As with FIGS. 10B and 10C, FIG. 10A is perforated by through holes 109. These through holes 109 have no bearing on the detection of a disbond. FIG. 10B illustrates a processed image 101 using the same sample of FIG. 10A and the system of FIG. 1. FIG. 10C illustrates a processed thermal image 105 using the system 50 with two flash heat lamps and the sample of FIG. 10A. The bonding is breached in one location and this breach is illustrated only in FIG. 10C.

The aluminum sample was not shiny but dull from small surface abrasions. The sample was 0.066 centimeters thick and the areas with the bonded metal were 0.145 centimeters thick. The measurement parameters were 120 frames acquired at a camera frame rate of 60 Hertz. The processed thermal image 105 was produced using the same temperature normalization data reduction routine used to produce image 101 of FIG. 10B. The dark areas in FIG. 10B mask the ability of the thermal inspection to reveal the disbanded portion of the sample. Instead, processed image 101 illustrates the unwanted superposition of the flash lamp effects 102. On the other hand, processed image 105 of FIG. 10C illustrates a disbond area 107 without the unwanted effects of the flash heat lamps. The SESS helps to image the disbond defect and the underlying structure of the stiffened panel as illustrated in FIG. 10C. The disbond area in FIG. 10C is illustrated by noting that the bottom half of FIG. 10C has alternating light and dark patches 108. These alternating patches 108 are absent in the top half of FIG. 10C, particularly in the circled region 107, indicative of an area of disbond.

We now turn our description to through-transmission setups and measurements, wherein the detector and heat source are located on opposite sides of the test sample. A through-transmission system 110 is shown in FIG. 11. A sample 111 having two opposing surfaces 112a and 112b, respectively, is situated between infrared detector 115 having lens 116 pointed at surface 112a of sample 111 and two flash lamps 113a and 113b, having reflectors 113x and 113y, respectively, pointed at surface 112b of sample 111. A computer 118 having a central processing unit 119 is electrically connected to lamps 113a and 113b, and is also connected to an image processor 117, which, in turn, is electrically connected to infrared detector 115. Although this system 110 for through transmission has two lamps, through transmission is often conducted using only one lamp if the sample size is small enough.

One problem encountered by the related art concerns small samples, where the reflector of one lamp used for through transmission is often bigger than the sample, causing radiation to pass around the sample and into the lens of the infrared detector. Further complicating this scenario, the radiation that passes around a small sample is usually of a much stronger intensity than the infrared radiation emanating from surface 112a into infrared detector 115, resulting in poor superimposed images. This problem is called "bleedover." Bleedover is particularly difficult when trying to measure small changes in temperature at the edge of a sample being inspected and can give a false indication of an increase in temperature at the edge of the test sample.

FIG. 12 illustrates an embodiment for through-transmission comprising system 120 using the SESS in accordance with the present invention. Sample 121 has one surface 122a facing a lens 125b of infrared detector 125a while the opposing surface 122b of sample 121 faces reflectors 123x and 123y of lamps 123a and 123b, respectively. In SESS through-transmission, the lamps 123a and 123b have shutters 124a and 124b, respectively, that can cover and uncover reflectors 123x and 123y, respectively. For system 120, infrared detector 125a with lens 125b also has a shutter 124c that can cover or uncover lens 125b. SESS through-transmission system 120 also has shutter control electronics 126 that operate the shutters 124a, 124b and 124c as well as control the firing of lamps 123a and 123b. As with SESS single-sided measurements, through-transmission measurement synchronization compensates for the finite amount of time to open and close a shutter after a signal has been sent, while the firing of the lamps is instantaneous and simultaneous with the signal to prompt the firing. As will be discussed later, the opening and closing of shutters 124a and 124b are complements of the closing and opening of shutter 124c as the shutter operation is synchronized. System 120 comprises an image processor 127 that takes raw temperature data over time from infrared detector 125a and processes it to uncover defects. The image processor 127 and the shutter control electronics 126 are generally controlled by a computer 128 having a central processing unit 129 electrically connected thereto. Although system 120 depicts two lamps, another embodiment may use only one lamp instead of two, depending on the size of the sample under test. With the arrangement of FIG. 12, if sample 121 is smaller than either reflector 123x or 123y, unwanted radiation from the lamps will not reach lens 125b because shutters 124a, 124b and 124c operate in such a way as to allow lens 125b to receive only infrared radiation radiating from surface 122a of sample 121. The timing diagrams for the opening and closing of each shutter along with the shutter electronics will be discussed later in the discussion of FIGS. 14 and 15.

Figure 13A:
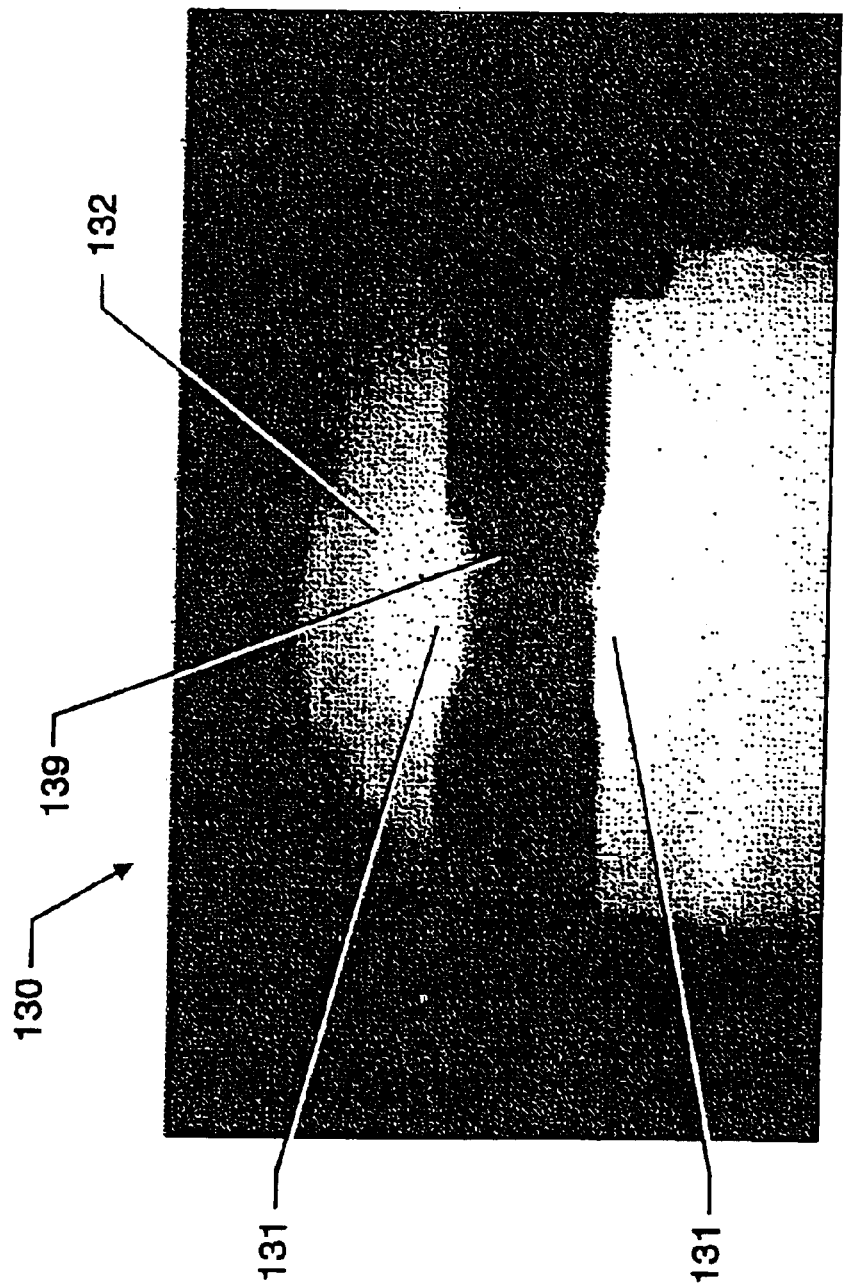
FIG. 13A is the temperature image acquired by the system of FIG. 11 using only one flash lamp with a filter permanently covering the flash heat lamp.

FIG. 13A illustrates a temperature image of a graphite epoxy sample having the dimensions of 2.54 cm by 12.7 cm with a thickness of 0.20 cm. Sample 139 is used to form the images of FIGS. 13B–13E. The system of FIG. 11, using only one flash heat lamp and a filter to cover the lamp, was employed to achieve the temperature image 130 of FIG. 13A. As with FIG. 4A, FIG. 13A suffers from the filter heating up during the firing of the flash and thereby superimposing unwanted infrared radiation from the hot filter after the firing of the lamp. The error created in FIG. 13A is more severe than the error superimposed in FIG. 4A because the superimposed, unwanted radiation emanating from the filter in FIG. 4A must reflect off the sample surface to get into the lens of the infrared detector, while no reflection is needed for unwanted radiation emanating from the filter in the case of FIG. 13A. This effect is even greater if the filter is removed.

The bleedover effect 131 in FIG. 13A is also caused by the fact that the sample size is smaller than the reflector of the lamp. Thus, the infrared detector does not experience a total eclipse of the lamp, nor the hot filter 132, by the sample. Custom made baffles at the edge of the sample can be used to block the infrared heat radiating from the lamps. Sometimes a baffle is placed on the lamp itself to block the residual heat radiation from the lamp.

Because the graphite epoxy composite sample 139 in FIGS. 13A–13E is a thermal insulator having a low thermal conductivity, processing is achieved by taking approximately 30 frames of temperature images, and applying these images to a curve fitting routine discussed below to achieve the processed thermal diffusivity images. If the bleedover radiation is not totally blocked, then the processed data will have errors, as shown in FIG. 13B, when using the system 110. No filter was used during sampling for the processed image of FIG. 13B. The processed diffusivity image 133 has dark areas 134 near the edge of the sample where the model did not converge for a valid diffusivity value. This failure to converge is because the size of the sample was smaller than the reflector of the lamp, causing the bleedover.

Using a filter helped in the modified setup of just one flash heat lamp, but still the values of thermal diffusivity were not obtained along the edges where the lamp and filter were directly behind the sample as illustrated in processed image 135 of FIG. 13C. FIG. 13C is a processed image of 30 temperature frames like FIG. 13A and undergoes the same processing as used to produce FIG. 13B. As with same side setup, the filter heats up during the firing of a flash lamp. Therefore, because the reflector of the lamp, and hence the filter, are larger than the sample size, the filter will emit unwanted infrared radiation that is superimposed with the infrared radiation radiating on the detector side of the sample and will cause erroneous thermal inspection results. Such erroneous results can be seen as the dark patches 136 along the edges where the measurements fail to converge with the theoretical model discussed below. Once again, FIG. 13C is another case of bleedover.

FIG. 13D employs the SESS system 120, using only one flash lamp and the sample used of FIG. 13A. Notice that there is no bleedover as the normalized, processed image 138 of FIG. 13D converges, even at the edges of the sample, with the theoretical model of equation 1 below for thermal diffusivity:

$$T_N(t) = \left(1 + 2\sum_{n=1}^{\infty} (-1)^n \text{Exp}\left[\frac{-n^2\pi^2\alpha t}{l^2}\right]\right) \quad (1)$$

where $T_N(t)$ is the normalized temperature response, the fit parameter is a which is the thermal diffusivity, l is the known thickness, and t is time. The diffusivity image without the shutter contains errors. The diffusivity values are saturated near the edge of the sample when SESS is not employed. The diffusivity image of the composite sample using the SESS is more defined on the edges. By using the SESS, measurement errors of thermal diffusivity along the edge are reduced. FIG. 13E illustrates how a processed image yields thermal diffusivity between 0.000 and 0.005 cm$^2$/sec depending on gray scale values of different parts of the processed images of FIGS. 13B, 13C and 13D.

Figure 14:
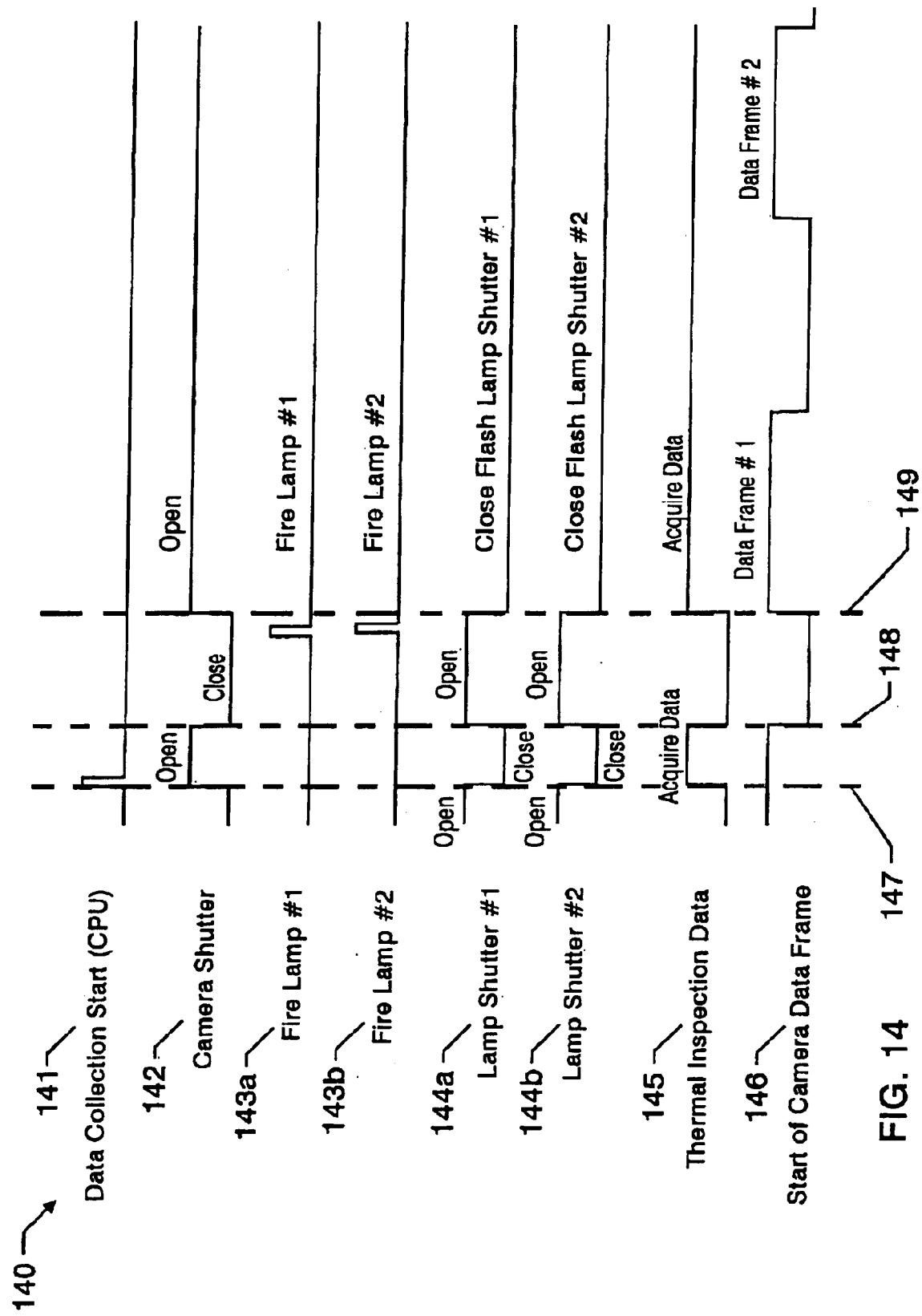
FIG. 14 is a timing diagram of the SESS embodiments of FIGS. 5 and 12 in accordance with the present invention.

A timing control diagram 140 and the steps for operation of the SESS for either the same-side thermal inspection system 50 or for the through-transmission thermal inspection system 120 are illustrated in FIG. 14. The start of data collection begins at step 141 when a trigger signal from the computer indicates the start of an inspection at time 147. This signal is used to trigger the detector shutter to open for an adjustable period of time at step 142 to allow for acquisition of background images. Step 142 also comprises the closing of the shutter to the detector at the same time 148 that the steps 144a and 144b of opening the lamp shutters begin. These shutter operations are done well in advance of the firing of the lamps because there is a mechanical delay between when the signal is sent and when the shutter is either fully opened or fully closed. During the opening of the lamp shutters, the lamps are fired at steps 143a and 143b with a duration of 0.008 seconds. Note that between the time 148 and the time 149, the shutter covering the lens prevents unwanted radiation from the lamp from entering the lens, either directly as through transmission or by reflection off the sample under test during same-side thermal inspection. The temperature of the sample under test generally raises about 10 degrees Celsius above ambient temperature for a 0.008 second flash. Shortly after the lamps fire, the shutters to the lamps close at steps 144a and 144b at the same time 149 that the shutter to the infrared detector is opened again at step 142. Now the detector can collect temperature images for thermal inspection at step 145 by measuring the infrared radiation emitted by the cooling of the sample. Because the shutters to the lamps were not covering the lamps when they were fired at steps 143a, 143b, the shutters do not emit unwanted infrared radiation into the infrared detector.

A mechanical delay occurs both when the detector shutter and lamp shutters open and when they close. The delays are approximately the same for both these shutters. They are calibrated to 60 Hertz. The time delay between sending a signal to open and close the shutters and the firing of the lamps is adjustable to account for the delay between the triggering of the shutters and the time when the shutters are fully opened or closed. The mechanical operation of opening and closing of the shutters should be completed before a signal to trigger the firing of the lamps is output as there is no or little time delay between the output of the lamp firing signals and the actual firing of the lamps.

Figure 15:
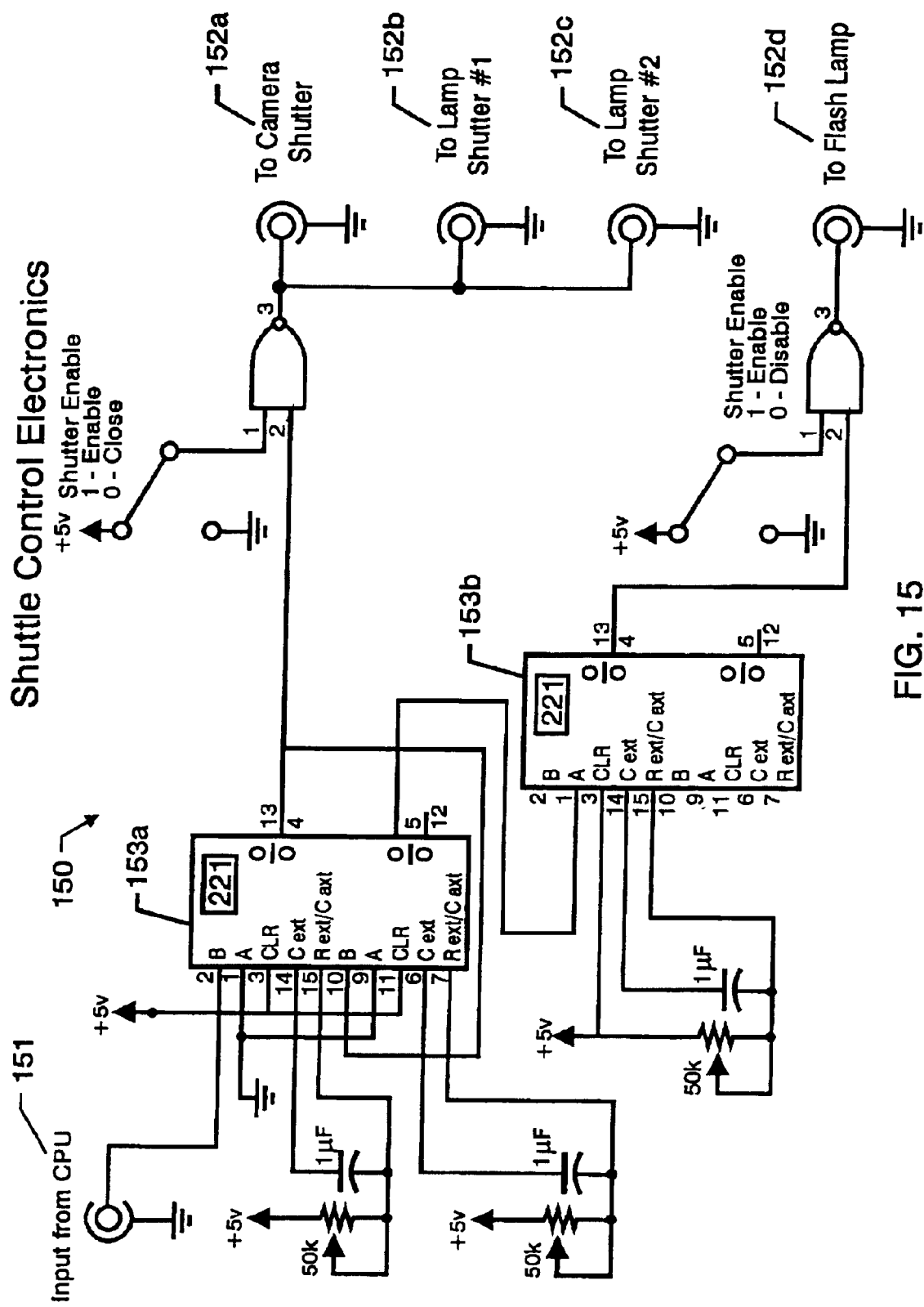
FIG. 15 is a schematic diagram of the electronic components of an SESS embodiment to enable the shutters to open and close and to fire the flash lamps according to the timing diagrams of FIG. 14.

The shutter control electronics 150 for operating the shutters and firing the lamps for the SESS of FIG. 5 (system 50) and of FIG. 12 (system 120) are illustrated in FIG. 15. The electronics 150 comprise one input signal 151 and four output signals 152a, 152b, 152c and 152d. The one input signal is a Transistor Transistor Logic (TTL) signal from the computer to indicate the start of the inspection. The rising edge of this pulse is used to generate four TTL output signals using two LS221 dual monostable multivibrators with Schmitt-trigger inputs 153a and 153b. The detector shutter 152a and lamp shutter signals 152b and 152c are complements of each other. During heating, the lamp shutters are open and the detector shutter is closed. During data collection by the detector, the detector shutter is open and the lamp shutters are closed. The lamp TTL trigger signal 152d is generated from the rising edge of the detector shutter signal. Both the shutters used for the detector and lamps have operating speeds on the order of the camera frame rate of 60 Hertz.

Referring now to FIG. 16, another embodiment of a synchronized electronic shutter system (SESS) 160 in accordance with the present invention is shown for single-sided inspection. The system 160 is similar to the system 50, but system 160 comprises a single shutter 164 for covering lens 165b of infrared detector 165a. In addition, system 160 comprises shutter electronics 166 that control the timing of the opening and the closing of the shutter 164 along with the timing of firing a first means for heating 163a and a second means for heating 163b (if used). The synchronization of system 160 involves the timing of the detector shutter 164 mechanically opening and then closing before the firing of the means for heating 163a, 163b. The system 160 has no delay, however, between sending a signal to fire a means for heating and the actual firing of it. The shutter electronics 166 are essentially the same electronics of the system described in FIG. 15, with the exception that the lamp shutter signals 152b, 152c are no longer required.

Both reflectors 163x, 163y are pointed at surface 162a of sample 161. Infrared detector 165a has a lens 165b that is also pointed at surface 162a of sample 161 and covered by shutter 164. The system 160 has an image processor 167 electrically connected to computer 168 having a central processing unit 169 to convert temperature images gleaned from infrared detector 165a into a processed image that illustrates the corrosion, defects, disbonding, delamination, or paint thickness of sample 161.

The first and second means for heating 163a, 163b may comprise a first flash heat lamp and a second flash heat lamp. Alternatively, the means for heating may comprise a quartz lamp or other heat source capable of heating the sample under test 161 to a temperature above ambient temperature in quick fashion. The shutter 164 may comprise one of a variety of mechanical structures, including a roller blind with a slot, a rotating disc with a slot, an iris diaphragm, a circular eyelid device, a set of movable vanes, or any other device capable of obstructing the transmittal of light waves along a directed path. The shutter 164 may be made of a reflective material and may also be made of a material having with low-emissivity properties.

The system 160 operates as follows. Before firing the lamps, 163a and 163b, the shutter 164 over the detector 165a is opened to acquire the necessary background data frame for offset calibration. During flash heating, the shutter 164 over the detector is closed to prevent the photons from the high intensity lamp from entering the infrared detector and lamps 163a and 163b are then fired. The flash heating duration is short (about 0.008 seconds) and heats the sample 161 under test by approximately 10 degrees Celsius above the ambient temperature. Immediately after the lamps 163a and 163b are fired, the detector shutter 164 is opened to measure the surface temperature. This shuttering and data collecting process is synchronized to the start of the acquisition of the next detector data frame. The shutter 164 is synchronized electronically with the lamps to close when the lamps are fired and open again after firing for data collection by the detector 165a.

FIG. 17 illustrates another embodiment of a synchronized electronic shutter system (SESS) 170 in accordance with the present invention for a through-transmission set-up system 170. Sample 171 has one surface 172a facing a lens 175b of infrared detector 175a while the opposing surface 172b of sample 171 faces reflectors 173x and 173y of lamps 173a and 173b, respectively. For this SESS through-transmission set-up, the system 170 has a single shutter 174 that can cover or uncover lens 175b. The SESS through-transmission system 170 also has shutter control electronics 176 that operate the shutter 174 as well as control the firing of lamps 173a and 173b. As with SESS single-sided measurements, through-transmission measurement synchronization compensates for the finite amount of time to open and close a shutter after a signal has been sent, while the firing of the lamps is instantaneous and simultaneous with the signal to prompt the firing. As with the system 160, the opening and closing of shutter 174 synchronizes with the firing of lamps 173a, 173b. System 170 comprises an image processor 177 that takes raw temperature data over time from infrared detector 175a and processes it to uncover defects. The image processor 177 and the shutter control electronics 176 are generally controlled by a computer 178 having a central processing unit 179 electrically connected thereto. Although system 170 depicts two lamps, another embodiment may use only one lamp instead of two, depending on the size of the sample under test. With the arrangement of FIG. 17, if sample 171 is smaller than either reflector 173x or 173y, unwanted radiation from the lamps will not reach lens 175b because shutter 174 operates in such a way as to allow lens 175b to receive only infrared radiation radiating from surface 172a of sample 171. The shutter electronics for system 170 are similar to the system 160. In other words, the shutter electronics 176 are essentially the same electronics of the system described in FIG. 15, with the exception that the lamp shutter signals 152b, 152c are no longer required.

Figure 18:
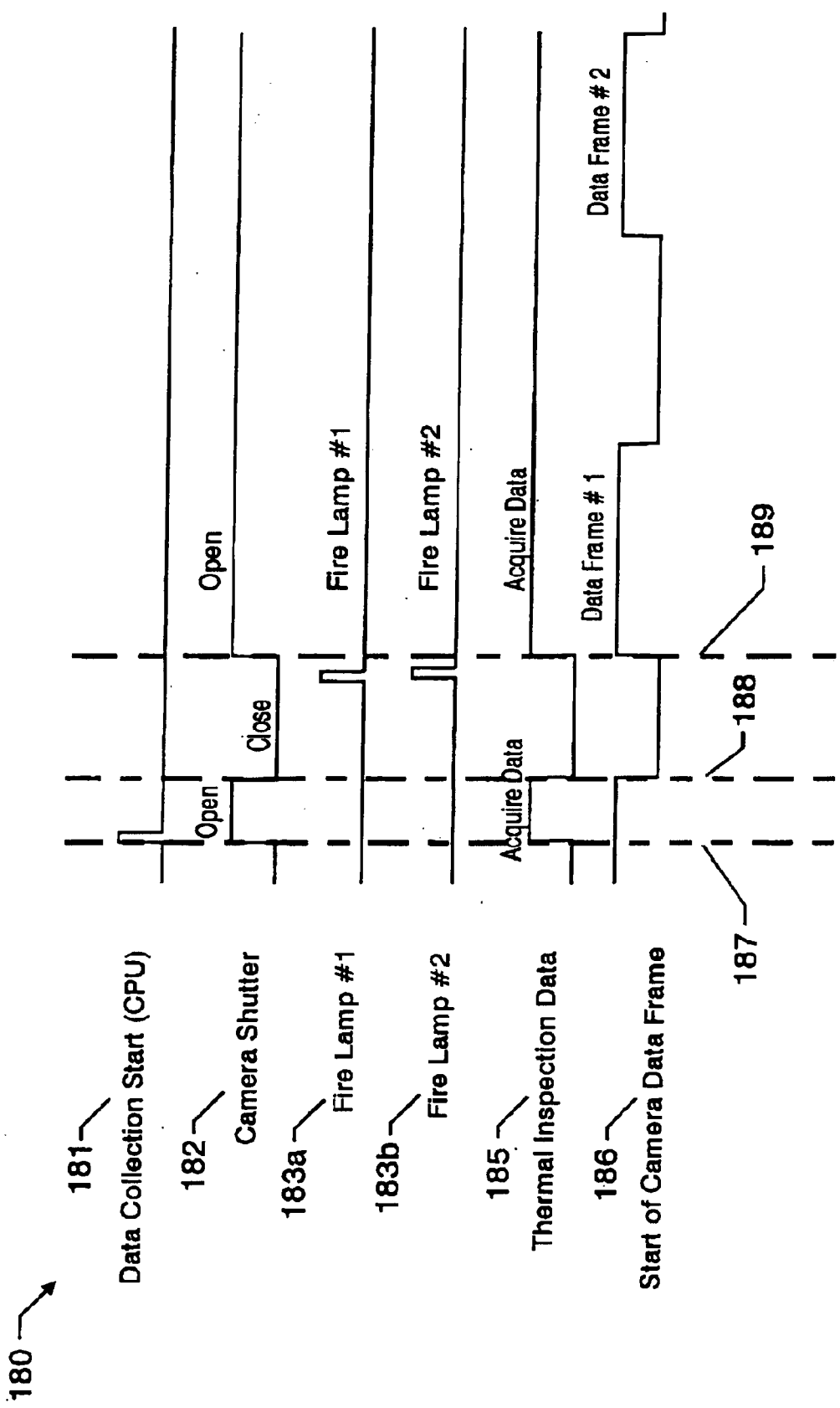
FIG. 18 is a timing diagram of the SESS embodiments of FIGS. 16 and 17.

The timing diagram and the acts of the method for thermal inspection for either the same-side thermal inspection system 160 or for the through-transmission thermal inspection system 170 are shown in FIG. 18. The timing control diagram is referenced generally as numeral 180. In thermal inspection systems, a trigger signal can be obtained from the computer to indicate the start of the step for collection of data 181 at time 187. This signal is used to trigger the detector (camera) shutter to open for an adjustable period of time at step 182 to allow for acquisition of background images. The shutter to the detector is then closed at the time 188. This shutter operation is done in advance of the firing of the lamps because the shutter has a mechanical delay between when the signal is sent to close the shutter and when the shutter is fully closed. After time 188, the lamps are fired at steps 183a and 183b with a duration of 0.008 seconds, with the shutter covering the detector lens preventing unwanted radiation from the flash from entering the lens, either directly during through-transmission or by reflection off the sample under test during same-side thermal inspection. The temperature of the sample under test generally raises about 10 degrees Celsius above ambient temperature for a 0.008 second flash. Shortly after the lamps fire, the step of collecting thermal inspection data 185 occurs by opening the shutter to the detector at time 189, which is after the lamps have fired. The detector takes temperature images by measuring the infrared radiation emitted by the cooling of the sample. The method of thermal inspection then repeats the steps 182 through 185 as described at step 186 until the desired number of data frames are acquired and processed.

A mechanical delay occurs both when the detector shutter opens and when it closes. The shutter is calibrated to 60 Hertz. The time delay between sending a signal to open and close the shutter and the firing of the lamps is adjustable to account for the delay between the triggering of the shutter and the time when the shutter is fully opened or closed. The mechanical operation of opening and closing of the shutter should be completed before a signal to trigger the firing of the lamps is output as there is no or little time delay between the output of the lamp firing signals and the actual firing of the lamps.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function and step-plus-function clauses are intended to cover the structures or acts described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed as new and desired to be secured by Letters Patent of the United States is:

1. A method for thermal inspection of a sample of material, said method comprising the steps of:
   pointing an infrared detector having a lens at a surface of said sample to acquire background data;
   covering said lens with a first shutter;
   firing a lamp having a reflector pointed at said sample to heat said sample above an ambient temperature;
   covering said lamp with a second shutter; and
   opening said first shutter to expose said lens to enable said detector to acquire temperature measurements of said sample over time as said sample cools down.

2. The method of claim 1, further comprising the step of opening said second shutter to expose said lamp while covering said lens with said first shutter.

3. The method of claim 1, wherein said step of covering said lamp with said second shutter occurs at the same time as said step of opening said first shutter to expose said lens of said infrared detector.

4. The method of claim 1, further comprising the step of receiving a signal from a computer to start said method before covering said lens of said infrared detector.

5. The method of claim 1, wherein said lamp and said infrared detector are on the same side of said sample.

6. The method of claim 5, wherein a second lamp resides on said same side of said sample as said first lamp and said infrared detector, said second lamp having a third shutter that covers said second lamp when said second shutter covers said first lamp and said third shutter uncovers said second lamp when said second shutter uncovers said first lamp, both said first lamp and said second lamp being pointed at a same surface of said sample as said infrared detector.

7. The method of claim 6, wherein one electronic input signal is input from a computer having a central processing unit that generates 4 electronic output signals, the first output signal being used for operating said first shutter, the second output signal being used for operating said second shutter, the third output signal being used for operating said third shutter, and the fourth output signal being used for triggering the firing of flashes from both said lamps simultaneously.

8. The method of claim 1, wherein said lamp is on an opposite side of said sample from said infrared detector.

9. The method of claim 1, wherein said first lamp has a duration of firing of approximately 0.002 seconds to raise a temperature of said sample approximately 10 degrees Celsius above an ambient temperature.

10. The method of claim 1, wherein said temperature measurements comprise a plurality of temperature images of said sample over time, said method further comprises the step of creating a processed image from said plurality of temperature images by a method selected from the group consisting of curve fitting for thermal diffusivity, time derivative calculations, normalization data reduction routine, and averaging.

11. An apparatus for thermally inspecting a sample of a material, comprising:
    an infrared detector having a lens pointed at a surface of said sample;
    means for heating said sample to a temperature above an ambient temperature;
    a first shutter to cover and uncover said lens of said infrared detector;
    a second shutter to cover and uncover said means for heating;
    shutter electronics, operatively connected to said first shutter and said second shutter, for controlling synchronization of the opening and closing of each shutter and a timing of a firing of said means for heating;
    a computer, electrically connected to said shutter electronics, for generating a trigger signal to initiate a thermal inspection process.

12. The apparatus of claim 11, wherein said means for heating is a flash heat lamp.

13. The apparatus of claim 12, further comprising a second flash heat lamp having a third shutter that moves in tandem to said second shutter.

14. The apparatus of claim 13, wherein said first and second flash heat lamps are both pointed at the same surface of said sample as said lens.

15. The apparatus of claim 11, wherein said shutter electronics cause said first shutter to uncover said infrared detector lens at the same time said second shutter covers said means for heating.

16. The apparatus of claim 11, wherein said shutter electronics cause said first shutter to cover said infrared detector lens at the same time said second shutter uncovers said means for heating.

17. The apparatus of claim 11, wherein said means for heating is pointed at a surface of said sample that is opposite to the surface said lens is pointed towards.

18. The apparatus of claim 11, wherein said shutter electronics comprise a pair of dual monostable muitivibrators.

19. The apparatus of claim 18, wherein each one of said pair of dual monostable multivibrators comprise Schmitt-trigger inputs.

20. The apparatus of claim 11, wherein said computer collects a plurality of temperature images over time taken by said infrared detector of said sample, said plurality of temperature images being used to construct a processed image by using a method selected from the group consisting of curve fitting for thermal diffusivity, time derivative calculations, normalization data reduction routine, and averaging.

21. A method for thermally inspecting a thin sample having a first surface and a second surface opposite to said first surface, said method comprising the steps of:
    opening a shutter to an infrared detector, said detector being pointed toward said first surface, to measure reference infrared radiation emanating from said first surface when said sample is at an ambient temperature;
    closing said shutter to said detector while opening a shutter of a lamp that is pointed at said sample;
    firing said lamp to heat said sample to a temperature above said ambient temperature;
    closing said shutter of said lamp to cover said lamp while opening said shutter to said infrared detector;
    acquiring a plurality of temperature images of said sample over time from said infrared detector; and
    producing a processed image from said plurality of temperature images.

22. The method of claim 21, wherein said processed image indicates a location where said first surface has a defect.

23. The method of claim 21, wherein said processed image is formed by a normalization data reduction routine performed on said plurality of temperature images and wherein said lamp is on a same side of said sample as said infrared detector.

24. The method of claim 23, further comprising the step of pointing said lamp at said first surface of said sample.

25. The method of claim 24, further comprising the step of pointing a second lamp toward said first surface, said second lamp comprising a shutter that operates in tandem to said shutter of said first lamp and said second lamp being fired at the same time said first lamp is fired.

26. The method of claim 21, wherein said processed image is formed by curve fitting said plurality of temperature images to a theoretical model for thermal diffusivity.

27. The method of claim 22, wherein said processed image is formed by applying a temperature normalization data reduction routine to said plurality of temperature images.

28. The method of claim 21, wherein said lamp is pointed at said second surface of said sample.

29. The method of claim 21, wherein said step of firing said lamp lasts for a duration of approximately 0.008 seconds and heats said sample approximately 10 Celsius degrees above said ambient temperature.

30. An apparatus for thermally inspecting a thin sample having a first surface and a second surface opposite to said first surface, comprising:
    an infrared detector having a lens pointed at said first surface, said detector having a first shutter;
    a lamp for heating said thin sample, said lamp having a reflector and having a second shutter, said lamp being pointed at one of said first surface and said second surface of said thin sample; and
    shutter electronics, operatively connected to said first shutter and said second shutter, for controlling synchronization of the opening and closing of each shutter to enable thermal inspection of said sample upon actuation of a trigger signal.

31. The apparatus of claim 30, said shutter electronics comprising a pair of dual monostable multivibrators with Schmitt-trigger inputs.

32. The apparatus of claim 30, said shutter electronics actuating said first and said second shutter in complement to one another.

33. The apparatus of claim 30, wherein said lamp is pointed at said second surface.

34. The apparatus of claim 30, further comprising a second lamp being pointed at said first surface, wherein said first lamp is also pointed at said first surface.

35. The apparatus of claim 30, further comprising a computer electrically connected to both an image processor and said shutter electronics, said computer actuating said trigger, said image processor receiving a plurality of temperature images of said sample taken over time by said infrared detector and applying one of a curve fitting routine for thermal diffusivity, a time derivative calculation, a normalization data reduction routine, and an averaging routine to produce a processed image that has the capability of illustrating locations of defects on said sample.

36. A method for thermal inspection of a sample of material, said method comprising the steps of:
pointing an infrared detector having a lens at a surface of said sample to acquire background data;
covering said lens with a shutter;
firing a lamp having a reflector pointed at said sample to heat said sample above an ambient temperature; and
opening said shutter from said lens to enable said infrared detector to acquire temperature measurements of said sample over time as said sample cools down.

37. The method of claim 36, wherein said step of firing said lamp to heat said sample occurs at the same time as the step of covering said lens with said shutter.

38. The method of claim 36, further comprising the step of receiving a signal from a computer to start said method before covering said lens of said infrared detector.

39. The method of claim 36, wherein said lamp and said infrared detector are on the same side of said sample.

40. The method of claim 39, wherein a second lamp resides on said same side of said sample as said first lamp and said infrared detector, said second lamp firing to heat said sample at the same time as the step of covering said lens with said shutter, both said first lamp and said second lamp being pointed at a same surface of said sample as said infrared detector.

41. The method of claim 40, wherein one electronic input signal is input from a computer having a central processing unit that generates two electronic outputs, the first output signal for operating said shutter, the second output signal for triggering the firing of flashes from both said lamps simultaneously.

42. The method of claim 36, wherein said lamp is on an opposite side of said sample from said infrared detector.

43. The method of claim 36, wherein said lamp has a duration of firing of approximately 0.008 seconds to raise a temperature of said sample approximately 10 degrees Celsius above an ambient temperature.

44. The method of claim 36, wherein said temperature measurements comprise a plurality of temperature images of said sample over time, said method further comprising the step of creating a processed image from said plurality of temperature images by a method selected from the group consisting of curve fitting for thermal diffusivity, time derivative calculations, normalization data reduction routine, and averaging.

45. An apparatus for thermally inspecting a sample of a material, comprising:
an infrared detector having a lens pointed at a surface of said sample;
means for heating said sample to a temperature above an ambient temperature;
a shutter to cover and uncover said lens of said infrared detector;
shutter electronics, operatively connected to said shutter, for controlling synchronization of the opening and closing of said shutter and a timing of a firing of said means for heating; and
a computer, electrically connected to said shutter electronics, for generating a trigger signal to initiate a thermal inspection process.

46. The apparatus of claim 45, wherein said means for heating is a flash heat lamp.

47. The apparatus of claim 46, further comprising a second flash heat lamp that fires in tandem with said first flash lamp.

48. The apparatus of claim 47, wherein said first and second flash heat lamps are both pointed at the same surface of said sample as said lens.

49. The apparatus of claim 45, wherein said shutter electronics cause said shutter to cover said infrared detector lens during said time of firing of said means for heating.

50. The apparatus of claim 45, wherein said shutter electronics cause said shutter to open after said time of firing said means for heating to enable said infrared detector to detect the infrared energy emanating from said heated sample.

51. The apparatus of claim 45, wherein said means for heating is pointed at a surface of said sample that is opposite to the surface said lens is pointed towards.

52. The apparatus of claim 45, wherein said shutter electronics comprise a pair of dual monostable multivibrators.

53. The apparatus of claim 52, wherein each one of said pair of dual monostable multivibrators comprise Schmitt-trigger inputs.

54. The apparatus of claim 45, wherein said computer collects a plurality of temperature images of said sample taken over time by said infrared detector, said plurality of temperature images being used to construct a processed image by using a method selected from the group consisting of curve fitting for thermal diffusivity, time derivative calculations, normalization data reduction routine, and averaging.

55. A method for thermally inspecting a thin sample having a first surface and a second surface opposite to said first surface, said method comprising the steps of:
pointing an infrared detector having a lens at said first surface of said thin sample to measure reference infrared radiation emanating from said first surface when said sample is at an ambient temperature;
covering said lens with a shutter;
firing a lamp that is pointed at said sample to heat said sample to a temperature above said ambient temperature;
opening said shutter to said lens of said infrared detector;
acquiring a plurality of temperature images of said sample over time by using said infrared detector; and
producing a processed image from said plurality of temperature images.

56. The method of claim 55, wherein said processed image indicates a location where said first surface has a defect.

57. The method of claim 55, wherein said processed image is formed by a normalization data reduction routine performed on said plurality of temperature images and wherein said lamp is on a same side of said sample as said infrared detector.

58. The method of claim 57, further comprising the step of pointing said lamp at said first surface of said sample.

59. The method of claim 58, further comprising the step of pointing a second lamp toward said first surface, said second lamp being fired at the same time said first lamp is fired.

60. The method of claim 55, wherein said processed image is formed by curve fitting said plurality of temperature images to a theoretical model for thermal diffusivity.

61. The method of claim 55, wherein said processed image is formed by applying a temperature normalization data reduction routine to said plurality of temperature images.

62. The method of claim 55, wherein said lamp is pointed at said second surface of said sample.

63. The method of claim 55, wherein said step of firing said lamp lasts for a duration of approximately 0.008 seconds and heats said sample approximately 10 degrees Celsius above said ambient temperature.

64. An apparatus for thermally inspecting a thin sample having a first surface and a second surface opposite to said first surface, comprising:

an infrared detector having a lens pointed at said first surface;

a shutter to cover and uncover said lens of said infrared detector;

a lamp for heating said thin sample, said lamp having a reflector that is pointed at said sample, said lamp being pointed at one of said first surface and said second surface of said thin sample; and shutter electronics, electrically connected to said shutter and said lamp, for synchronizing the opening and closing of said shutter with a firing of said lamp such that said shutter covers said lens of said infrared detector during the time of firing of said lamp and said shutter opens when said lamp is not fired to enable thermal inspection of said sample.

65. The apparatus of claim 64, wherein said shutter electronics comprise a pair of dual monostable multivibrators with Schmitt-trigger inputs.

66. The apparatus of claim 64, said lamp being pointed at said second surface.

67. The apparatus of claim 64, further comprising a second lamp being pointed at said first surface, said first lamp also being pointed at said first surface.

68. The apparatus of claim 64, further comprising a computer electrically connected to both an image processor and said shutter electronics, said computer actuating a trigger signal from said shutter electronics to fire said lamp, said image processor receiving a plurality of temperature images of said sample taken over time by said infrared detector and applying one of a curve fitting routine for thermal diffusivity, a time derivative calculation, a normalization data reduction routine, and an averaging routine to produce a processed image that has the capability of illustrating locations of defects on said sample.

* * * * *